(12) United States Patent
Sekiya et al.

(10) Patent No.: US 9,213,014 B2
(45) Date of Patent: Dec. 15, 2015

(54) GAS SENSOR

(71) Applicant: NGK Insulators, Ltd., Nagoya (JP)

(72) Inventors: Takayuki Sekiya, Nissin (JP); Mika Murakami, Nagoya (JP); Tomoya Seimori, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 499 days.

(21) Appl. No.: 13/676,576

(22) Filed: Nov. 14, 2012

(65) Prior Publication Data

US 2013/0126352 A1    May 23, 2013

(30) Foreign Application Priority Data

Nov. 18, 2011  (JP) ................................. 2011-253165
Nov. 13, 2012  (JP) ................................. 2012-249206

(51) Int. Cl.
    *G01N 27/407*     (2006.01)
    *F01N 11/00*      (2006.01)
    *G01M 15/10*      (2006.01)

(52) U.S. Cl.
    CPC ............ *G01N 27/4077* (2013.01); *F01N 11/00* (2013.01); *G01M 15/10* (2013.01)

(58) Field of Classification Search
    CPC . G01M 15/10; G01M 15/102; G01M 15/104; G01N 1/2252; G01N 27/404–27/407; G01N 27/409; G01N 27/419; G01N 27/41; F01N 2560/00–2560/20; F01N 2550/00–2550/24; F01N 3/10; F01N 11/00
    See application file for complete search history.

(56) References Cited

U.S. PATENT DOCUMENTS

| | | | |
|---|---|---|---|
| 2008/0028831 A1 | 2/2008 | Nakashima et al. | |
| 2008/0236248 A1* | 10/2008 | Ikoma et al. | 73/23.31 |
| 2011/0036716 A1* | 2/2011 | Sekiya et al. | 204/424 |
| 2011/0126610 A1* | 6/2011 | Sekiya et al. | 73/25.05 |
| 2011/0283775 A1* | 11/2011 | Sekiya et al. | 73/31.05 |

FOREIGN PATENT DOCUMENTS

| | | |
|---|---|---|
| EP | 1 046 906 A2 | 10/2000 |
| EP | 1 471 346 A1 | 10/2004 |
| EP | 2 287 598 A1 | 2/2011 |
| EP | 2 333 534 A2 | 6/2011 |
| EP | 2 388 578 A2 | 11/2011 |
| JP | 60-58589 U | 4/1985 |

(Continued)

OTHER PUBLICATIONS

Extended European Search Report (Application No. 14157313.9) dated May 9, 2014.

(Continued)

*Primary Examiner* — Jennifer Dieterle
(74) *Attorney, Agent, or Firm* — Burr & Brown, PLLC

(57) ABSTRACT

In a gas sensor, a ratio A2/A1 defined by a ratio of an opening area A1 per first inner gas hole and an opening area A2 per second inner gas hole is set to higher than or equal to 0.9 and lower than or equal to 3.8 and, more preferably, to higher than or equal to 1.5 and lower than or equal to 1.9. Accordingly, adhesion of water to a sensor element can be sufficiently prevented. In addition, a ratio B2/B1 defined by a ratio of a total opening area B1 of the first inner gas holes to a total opening area B2 of the second inner gas holes is set to higher than or equal to 0.85 and, more preferably, higher than or equal to 1.5. Accordingly, adhesion of water to the sensor element can be more reliably, effectively prevented.

13 Claims, 27 Drawing Sheets

(56) References Cited

FOREIGN PATENT DOCUMENTS

| JP | 2000-304719 A1 | 11/2000 |
| JP | 2001-099807 A | 4/2001 |
| JP | 2011-038953 A | 2/2011 |
| JP | 2011-112557 A | 6/2011 |

OTHER PUBLICATIONS

European Search Report, European Application No. 12192777.6, dated Mar. 20, 2013 (with English Translation) (8 pages).
Japanese Notification, Japanese Application No. 2012-249206, dated Feb. 17, 2015 (9 pages).
Japanese Office Action (With English Translation), Japanese Application No. 2012-249206, dated Apr. 21, 2015 (7 pages).

* cited by examiner

FNNGA254

FNNGA254

FNNGA254

FNNGA254

FNNGA254

View on an arrow E

FNNGA254

FNNGA254

FNNGA254

GAS SENSOR

BACKGROUND OF THE INVENTION

1. Field of the Invention

The present invention relates to a gas sensor.

2. Description of the Related Art

Gas sensors that detect a predetermined concentration of a gas component, such as $NO_x$ or oxygen, contained in gas to be measured, such as exhaust gas of an automobile, have been widely known. In such gas sensors, water generated when an engine is started, for example, adheres to a sensor element and, therefore, the temperature of the sensor element decreases. Thus, cracking may occur in the sensor element. Therefore, to prevent the occurrence of cracking, it is proposed that a protective cover is attached to the sensor element so as to cover the sensor element. For example, PTL 1 describes a gas sensor including a sensor element having a protective cover on the outer periphery of the free end portion of the sensor element. The protective cover has a dual structure including a ventilation hole formed therein. The ventilation hole allows exhaust gas to enter the inside of the protective cover.

CITATION LIST

Patent Literature

[PTL 1] Japanese Unexamined Patent Application Publication No. 2000-304719 (FIG. 11)

SUMMARY OF THE INVENTION

However, even when such a protective cover having a dual structure is employed, water enters the inside of the protective cover and adheres to the sensor element, in some cases. Thus, the sensor element is cooled.

Accordingly, it is a primary object of the present invention to sufficiently prevent water from adhering to a sensor element.

The present inventors discovered that in a gas sensor having a dual structure, adhesion of water to the sensor element can be sufficiently prevented by controlling a ratio A2/A1 defined by a ratio of an opening area A1 per first inner gas hole formed in a portion of the inner protective cover adjacent to the base end of the sensor element and an opening area A2 per second inner gas hole formed in a portion of the inner protective cover adjacent to the free end of the sensor element so that the ratio A2/A1 is in a predetermined range. Thus, the goal of the present invention is achieved.

A gas sensor of the present invention comprises: a sensor element; an inner protective cover having a bottomed cylindrical shape, the inner protective cover having at least one first inner gas hole and at least one second inner gas hole formed therein and covering a top end of the sensor element; and an outer protective cover having a bottomed cylindrical shape, the outer protective cover having a plurality of outer gas holes formed therein and covering the inner protective cover; wherein the first inner gas hole is located so as to be closer to a base end of the sensor element than the second inner gas hole, and wherein a ratio A2/A1 defined by a ratio of an opening area A1 per first inner gas hole and an opening area A2 per second inner gas holes is higher than or equal to 0.9 and lower than or equal to 3.8.

In such a gas sensor including the protective cover having a dual structure, if the ratio A2/A1 is higher than or equal to 0.9 and lower than or equal to 3.8, adhesion of water to the sensor element can be sufficiently prevented. It is desirable that the ratio A2/A1 be higher than or equal to 1.5 and lower than or equal to 1.9. The ratio A2/A1 in this range can more effectively prevent adhesion of water to the sensor element. Note that the number of the first inner gas holes may be set to six. In addition, the number of the second inner gas holes may be set to a value in the range from 3 to 6. Furthermore, the first inner gas hole may serve as an inlet hole through which the gas to be measured flows into the inner protective cover, and the second inner gas hole may serve as an outlet hole through which the gas to be measured flows out of the inner protective cover.

In the gas sensor according to the present invention, it is desirable that a ratio B2/B1 defined by a ratio of a total opening area B1 of the first inner gas holes to a total opening area B2 of the second inner gas holes be higher than or equal to 0.85. The ratio B2/B1 in this range can reliably, effectively prevent adhesion of water to the sensor element. In addition, as the ratio B2/B1 increases, adhesion of water to the sensor element can be more effectively prevented. It is more desirable that the ratio B2/B1 be higher than or equal to 1.5. Note that the total opening area B2 may be greater than or equal to 1.55 $mm^2$ or greater than or equal to 2.8 $mm^2$.

In the gas sensor according to the present invention, it is desirable that a distance L between the center of the second inner gas hole and a bottom surface of the inner protective cover be less than or equal to 3 mm. The distance L in this range can more reliably, effectively prevent adhesion of water to the sensor element. In addition, as the distance L decreases, adhesion of water to the sensor element can be more reliably prevented. It is more desirable that the distance L be less than or equal to 2.2 mm. It is still more desirable that the distance L be less than or equal to 1.1 mm.

In the gas sensor according to the present invention, it is desirable that the outer protective cover be a cover having a side surface and a bottom surface, each of the outer gas holes be formed in a boundary portion between the side surface and the bottom surface of the outer protective cover, and an angle θ1 formed by an external opening plane of the outer gas hole and the bottom surface of the outer protective cover be in the range from 10° to 80°. In this manner, occurring of a variation of the responsiveness of the sensor element when the flow velocity of the gas to be measured varies can be further effectively prevented, as compared with the case in which the hole is located in the side surface or the case in which an angle formed by the external opening plane of the outer gas hole and the bottom surface of the outer protective cover is outside the range from 10° to 80°. That is, the flow velocity dependency of the responsiveness of the sensor element can be reduced. In addition, in this manner, water that entered the outer protective cover can be easily drained to the outside through the outer gas hole, as compared with the case in which the hole is located in the side surface or the case in which an angle formed by the external opening plane of the outer gas hole and the bottom surface of the outer protective cover is outside the range from 10° to 80°. Thus, entry of water into the outer protective cover and adhesion of water to the sensor element can be more effectively prevented.

In the gas sensor according to the present invention, it is desirable that the inner protective cover include a guide portion that regulates a flow of a gas to be measured flowing into the inner protective cover through the first inner gas hole, and a ratio R2/R1 defined by a ratio of a radius R1 representing a radius of a circumscribed circle of the sensor element, where the circumscribed circle is coaxial with the inner protective cover, to a radius R2 representing a radius of an inscribed circle of a plane including a regulation surface of the guide portion that regulates the flow of the gas to be measured, where the inscribed circle is coaxial with the inner protective cover, be higher than or equal to 1 and lower than or equal to 2.38. By setting the ratio R2/R1 to 1 or higher, the guide portion can prevent the gas to be measured that has passed through the first inner gas hole from flowing directly toward the sensor element. Thus, adhesion of water to the sensor element and cooling of the sensor element due to the flow of the gas to be measured can be more effectively prevented. In addition, by setting the ratio R2/R1 to 2.38 or lower, a sufficient opening area of the first inner gas hole can be obtained. Note that the radius R2 may be greater than or equal to the width of the sensor element times 0.55 and less than or equal to the width times 1.30.

In the gas sensor according to the present invention, it is desirable that the gas sensor be fixed to the inside of the pipe such that the center axis of the inner protective cover is tilted from a vertical direction at an angle θ2 (0°<θ2<90°) and, when the second inner gas hole is projected onto a plane perpendicular to the center axis of the inner protective cover, a minimum value θ3 of an angle formed by a line extending between the center of the second inner gas hole and the center of the inner protective cover and a vertical line obtained by projecting a line extending from the center of the inner protective cover in the vertical downward direction onto the plane be greater than or equal to 0° and less than 45°. As the minimum value θ3 is closer to 0°, the second inner gas hole is located in the inner protective cover closer to the vertically downward direction. Therefore, water is easily drained from the second inner gas hole. In this manner, adhesion of water to the sensor element can be more effectively prevented. It is more desirable that the minimum value θ3 be greater than or equal to 0° and less than or equal to 15°. Note that the gas sensor may be fixed to the inside of the pipe such that the center axis of the inner protective cover is perpendicular to the flow of the gas to be measured in the pipe and is tilted from the vertical direction at the angle θ2.

According to the present invention, it is desirable that the gas sensor in which the minimum value θ3 is greater than or equal to 0° and less than 45° further include a housing that is fixed to the inside of the pipe using a fixing member and that fixes the inner protective cover. A phase of the inner protective cover relative to the fixing member in the circumferential direction is defined so that the minimum value θ3 is set to a predetermined value by defining a fixed position of the housing relative to the fixing member using a pair of positioning portions, one formed in the housing and the other formed in the fixing member, and defining a fixed position of the inner protective cover relative to the housing a pair of positioning portions, one formed in the inner protective cover and the other formed in the housing. In this manner, by using the pair of positioning portions, one formed on the housing and the other formed on the fixing member, and the pair of positioning portions, one formed on the inner protective cover and the other formed on the housing, the minimum value θ3 can be easily set to predetermined value. Note that the pair of positioning portions may be formed from, for example, a pair consisting of a convex portion and a concave portion. By inserting the convex portion into the concave portion, position adjustment can be performed.

In the gas sensor according to the present invention, it is desirable that the gas sensor be fixed to the inside of the pipe such that the center axis of the inner protective cover is tilted from a vertical direction at an angle θ2 (0°<θ2<90°) and, when each of the outer gas holes is projected onto a plane perpendicular to the center axis of the outer protective cover, a minimum value θ4 of an angle formed by a line extending between the center of the outer gas hole and the center of the outer protective cover and a vertical line obtained by projecting a line extending from the center of the outer protective cover in the vertical downward direction onto the plane be greater than or equal to 0° and less than or equal to 30°. As the minimum value θ4 is closer to 0°, the outer gas hole is located in the outer protective cover closer to the vertically downward direction. Therefore, water is easily drained from the outer gas hole. In this manner, adhesion of water to the sensor element can be more effectively prevented. Note that the gas sensor may be fixed to the inside of the pipe such that the center axis of the inner protective cover is perpendicular to the flow of the gas to be measured in the pipe and is tilted from a vertical direction at the angle θ2.

According to the present invention, it is desirable that the gas sensor in which the minimum value θ4 is greater than or equal to 0° and less than or equal to 30° further include a housing that is fixed to the inside of the pipe using a fixing member and that fixes the outer protective cover. A phase of the outer protective cover relative to the fixing member in the circumferential direction is defined so that the minimum value θ4 is set to a predetermined value by defining a fixed position of the housing relative to the fixing member using a pair of positioning portions, one formed in the housing and the other formed in the fixing member, and defining a fixed position of the outer protective cover relative to the housing a pair of positioning portions, one formed in the outer protective cover and the other formed in the housing. In this manner, by using the pair of positioning portions, one formed on the housing and the other formed on the fixing member, and the pair of positioning portions, one formed on the outer protective cover and the other formed on the housing, the minimum value θ4 can be easily set to predetermined value. Note that the pair of positioning portions may be formed from, for example, a pair consisting of a convex portion and a concave portion. By inserting the convex portion into the concave portion, position adjustment can be performed.

The gas sensor of the present invention further comprises: a first gas chamber; and a second gas chamber; wherein the outer protective cover includes a cylindrical body portion having a plurality of gas passing holes formed therein, a bottomed cylindrical free end portion having a diameter that is smaller than that of the body portion, and a stepped portion that connects the body portion to the free end portion, and wherein each of the outer gas holes is a hole formed in the free end portion, and wherein the first gas chamber is surrounded by the body portion and the stepped portion of the outer protective cover and the inner protective cover, and the first gas chamber communicates with the inside of the inner protective cover through the first inner gas hole, and wherein the second gas chamber is surrounded by the free end portion of the outer protective cover and the inner protective cover, the second gas chamber does not directly communicate with the first gas chamber, and the second gas chamber communicates with the inside of the inner protective cover through the second inner gas hole.

In the gas sensor according to the present invention, the inner protective cover may include a cylindrical first body portion having the first inner gas hole formed therein, a cylindrical second body portion, a bottomed cylindrical free end portion having the second inner gas hole formed therein, a first stepped portion that connects the first body portion to the second body portion, and a second stepped portion that connects the second body portion to the free end portion, and a free end of the sensor element may be located in a space surrounded by the first body portion. In this manner, the free end of the sensor element is located closer to the first inner gas hole, as compared with, for example, the case in which the free end of the sensor element is located in a space surrounded by the second body portion of the inner protective cover or the free end portion of the inner protective cover. Thus, the responsiveness of the sensor element can be improved. Note that the first body portion, the second body portion, and the free end portion of the inner protective cover may be coaxial. In addition, the diameter of the second body portion may be smaller than that of the first body portion, and the diameter of the free end portion may be smaller than that of the second body portion.

DETAILED DESCRIPTION OF THE INVENTION

Figure 1A:
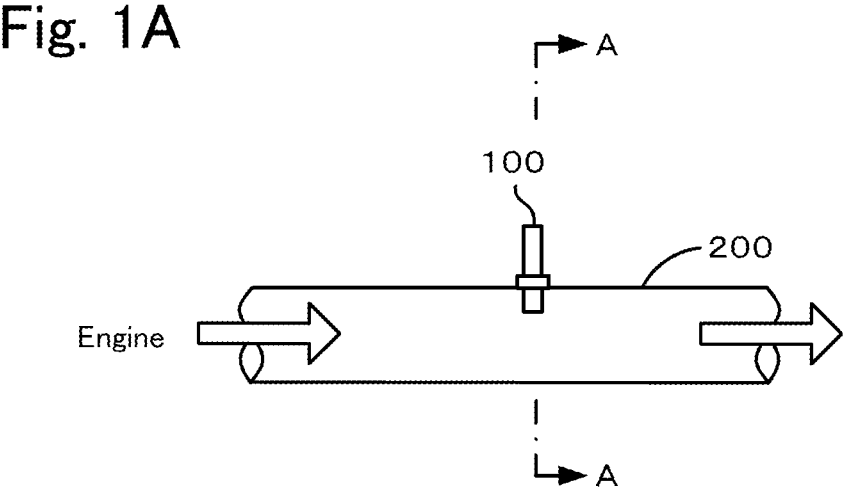
FIGS. 1A-1B are schematic illustrations of a gas sensor 100 attached to a pipe 200.
Figure 1B:
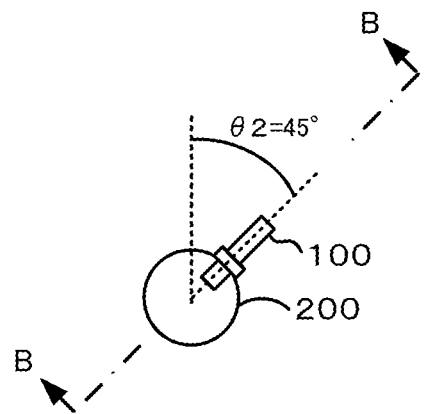
Figure 2:
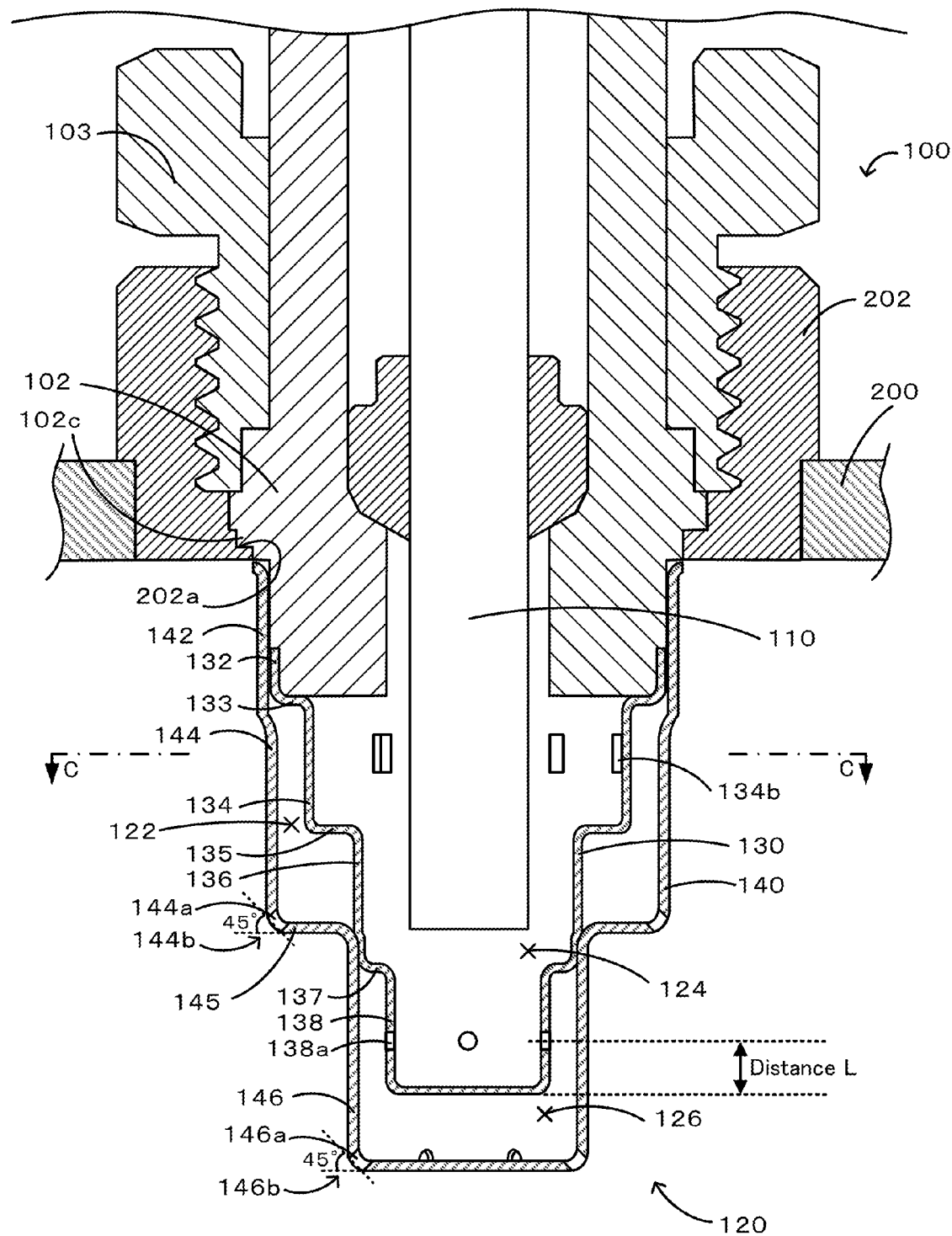
FIG. 2 is a cross-sectional view taken along a line B-B of FIG. 1B.
Figure 3:
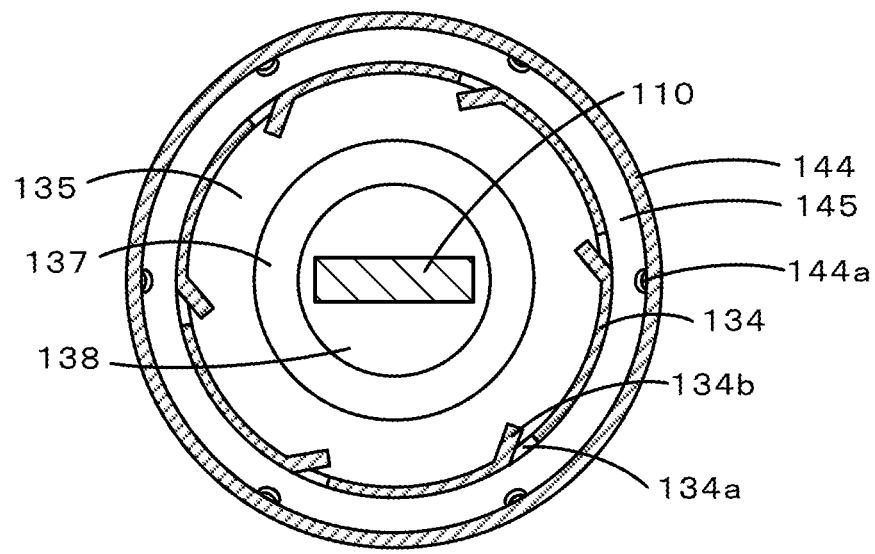
FIG. 3 is a cross-sectional view taken along a line C-C of FIG. 2.

Embodiments of the present invention are described next with reference to the accompanying drawings. FIGS. 1A-1B are schematic illustrations of a gas sensor 100 attached to a pipe 200. FIG. 1A is an illustration of the pipe 200 when viewed from the side, and FIG. 1B is a cross-sectional view taken along a line A-A of FIG. 1A. FIG. 2 is a cross-sectional view taken along a line B-B of FIG. 1B, and FIG. 3 is a cross-sectional view taken along a line C-C of FIG. 2. For convenience of description, FIG. 2 is an enlarged view of a portion of the cross section taken along the line B-B of FIG. 1B.

As illustrated in FIG. 1A, the gas sensor 100 is mounted in the pipe 200 serving as an exhaust path starting from the engine of a vehicle. The gas sensor 100 detects the concentration of at least one of gas components, such as $NO_x$ and $O_2$, contained in exhaust gas serving as the gas to be measured. As illustrated in FIG. 1B, the gas sensor 100 is fixed to the inside of the pipe 200 so that the center axis of the gas sensor 100 is perpendicular to the flow of gas to be measured in the pipe 200 and is tilted at an angle of $\theta 2$ with respect to the vertical direction. The angle $\theta 2$ is in the range of $0°<\theta 2<90°$. According to the present embodiment, the angle $\theta 2$ is 45°.

As illustrated in FIG. 2, the gas sensor 100 includes a sensor element 110 having a function of detecting the concentration of a gas component of gas to be measured and a protective cover 120 that protects the sensor element 110. In addition, the gas sensor 100 includes a metal housing 102 and a metal nut 103 having a male screw on the outer circumferential surface thereof. The housing 102 is inserted into a fixing member 202 that is welded to the pipe 200 and that has a female screw on the inner circumferential surface thereof. When the nut 103 is additionally inserted into the fixing member 202, the metal housing 102 is fixed to the fixing member 202. In this manner, the gas sensor 100 is fixed to the inside of the pipe 200.

The sensor element 110 has a shape of an elongated plate. The sensor element 110 is made of an oxygen ion conductive solid electrolyte layer, such as a zirconia ($ZrO_2$) layer. The sensor element 110 has a heater therein. The heater controls the temperature of the sensor element 110 by heating the sensor element 110 and maintains the temperature of the sensor element 110. The configuration of the sensor element 110 and the principle for detecting the concentration of a gas component are widely known. For example, the configuration and the principle are described in Japanese Unexamined Patent Application Publication No. 2008-164411.

The protective cover 120 is disposed so as to surround the periphery of the sensor element 110. The protective cover 120 includes a bottomed cylindrical inner protective cover 130 that covers the free end portion of the sensor element 110. The protective cover 120 further includes a bottomed cylindrical outer protective cover 140 that covers the bottomed cylindrical inner protective cover 130. In addition, a space formed between the inner protective cover 130 and the outer protective cover 140 serves as a first gas chamber 122 and a second gas chamber 126. A space surrounded by the inner protective cover 130 serves as a sensor element chamber 124. Note that the gas sensor 100, the inner protective cover 130, and the outer protective cover 140 are coaxial.

The inner protective cover 130 is formed from a metal member (e.g., a stainless steel member). The inner protective cover 130 includes a large-diameter portion 132 having a cylindrical shape, a first body portion 134 having a cylindrical shape with a diameter that is smaller than that of the large-diameter portion 132, a second body portion 136 having a cylindrical shape with a diameter that is smaller than that of the first body portion 134, and a free end portion 138 having a bottomed cylindrical shape with a diameter that is smaller than that of the second body portion 136. In addition, the inner protective cover 130 includes a stepped portion 133 that connects the large-diameter portion 132 to the first body portion 134, a stepped portion 135 that connects the first body portion 134 to the second body portion 136, and a stepped portion 137 that connects the second body portion 136 to the free end portion 138. Note that the large-diameter portion 132, the first body portion 134, the second body portion 136, and the free end portion 138 are coaxial. The inner circumferential surface of the large-diameter portion 132 is in contact with the housing 102. Thus, the inner protective cover 130 is fixed to the housing 102. The first body portion 134 and the second body portion 136 are located so as to cover the side surface of the sensor element 110. The first body portion 134 has six first inner gas holes 134a and six plate-like guide portions 134b formed therein (refer to FIG. 3). Each of the first inner gas holes 134a allows the first gas chamber 122 to communicate with the sensor element chamber 124. Each of the plate-like guide portions 134b regulates the flow of gas to be measured flowing into the sensor element chamber 124 through one of the first inner gas holes 134a. The first inner gas holes 134a are disposed at equal intervals, and the plate-like guide portions 134b are disposed at equal intervals. The side surface of the free end portion 138 has four second inner gas holes 138a formed at equal intervals. Each of the second inner gas holes 138a allows the sensor element chamber 124 to communicate with the second gas chamber 126.

Figure 4:
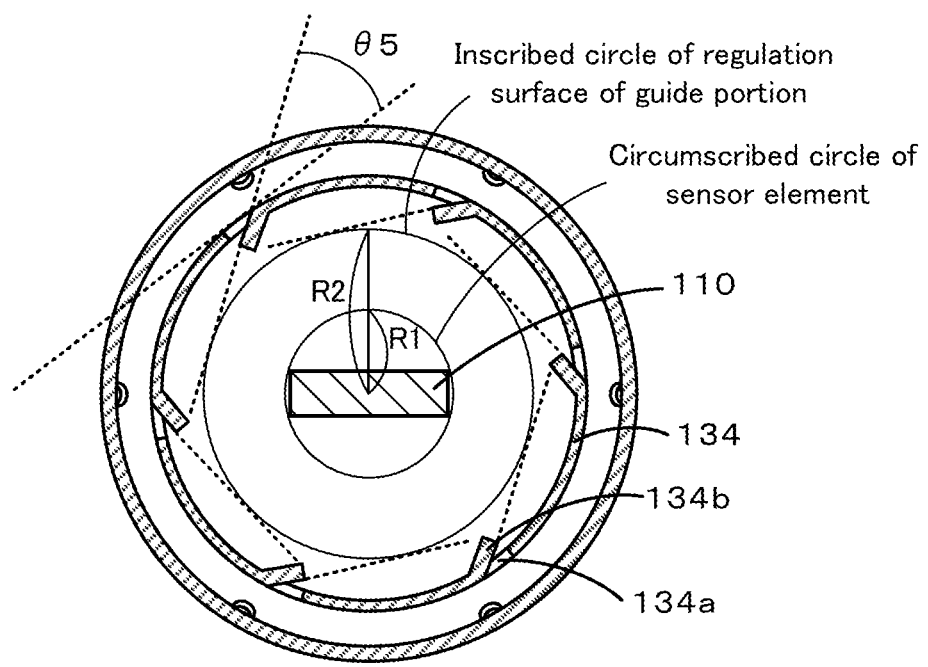
FIG. 4 illustrates a positional relationship among guide portions 134b and a sensor element 110.
Figure 5:
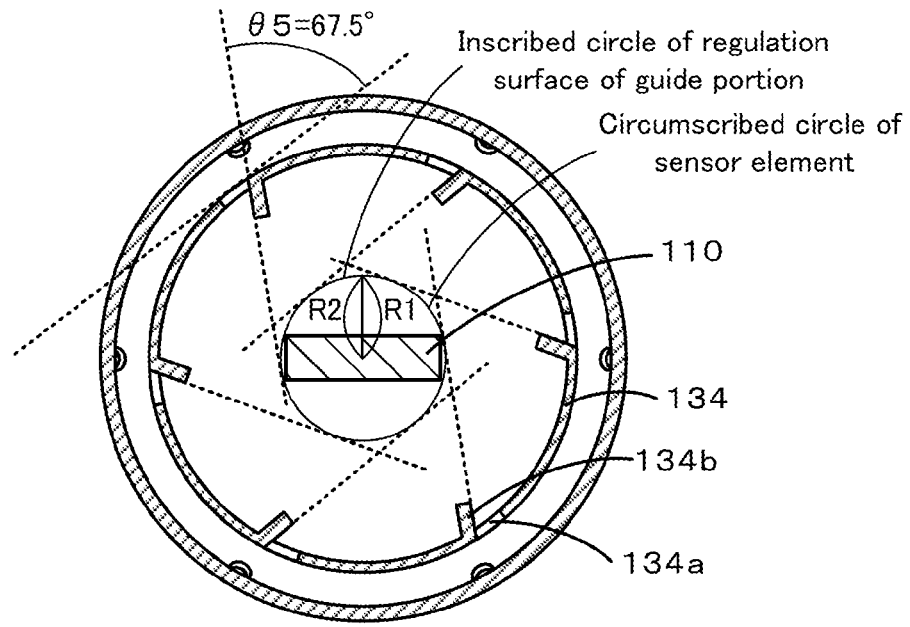
FIG. 5 illustrates a positional relationship among the guide portions 134b and the sensor element 110 when the ratio R2/R1 is a value of 1.
Figure 6:
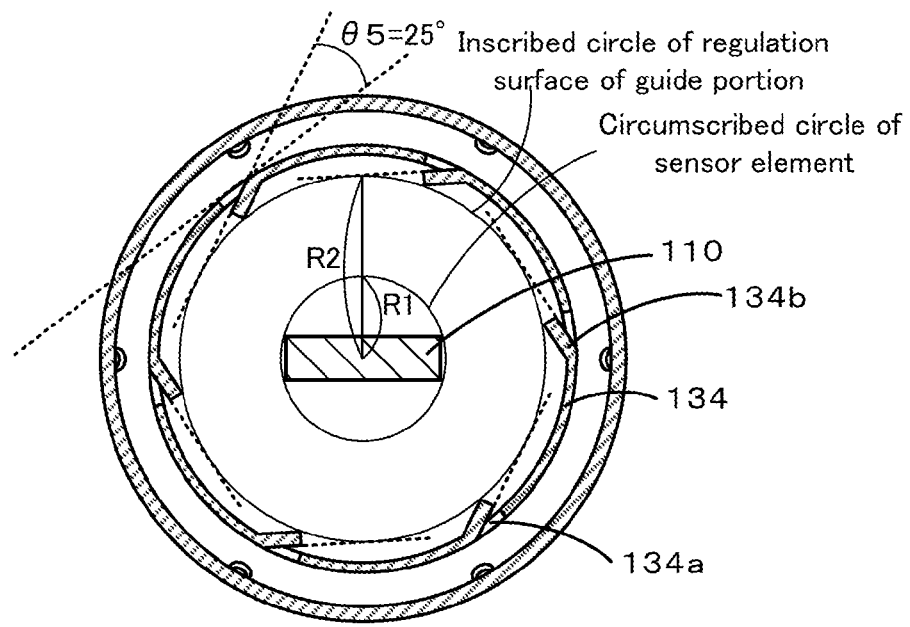
FIG. 6 illustrates a positional relationship between the guide portions 134b and the sensor element 110 when the ratio R2/R1 is a value of 2.38.

As illustrated in FIG. 3, the first inner gas holes 134a have one-to-one correspondence with the guide portions 134b. Each of the guide portions 134b is formed so as to be located between the corresponding first inner gas hole 134a and the sensor element 110. In addition, the guide portions 134b are formed so as to be rotationally symmetrical (6-fold rotational symmetry). FIG. 4 illustrates the positional relationship among the sensor element 110 and the guide portions 134b. As illustrated in the drawing, let R1 be the radius of a circumscribed circle of the sensor element 110 (the circle is coaxial with the inner protective cover 130), and let R2 be the radius of an inscribed circle of planes each including the regulation surface of one of the guide portions 134b that regulate the flow of the gas to be measured (the circle is coaxial with the inner protective cover 130). Then, according to the present embodiment, the guide portions 134b are formed so that a ratio R2/R1 is higher than or equal to 1 and lower than or equal to 2.38. By setting the ratio R2/R1 to 1 or higher, the guide portions 134b can prevent the gas to be measured that has passed through the first inner gas holes 134a from directly flowing toward the sensor element 110. Thus, adhesion of water to the sensor element 110 and cooling of the sensor element 110 due to the flow of the gas to be measured can be prevented. In addition, by setting the ratio R2/R1 to 2.38 or lower, a sufficient opening area of each of the first inner gas holes 134a can be obtained. Note that the term "opening area of the first inner gas hole 134a" refers to the opening area of the first inner gas hole 134a when viewed in a direction of the flow of the gas to be measured that passes through the first inner gas hole 134a. Accordingly, when the guide portion 134b is present, the opening area of the first inner gas hole 134a represents the opening area of the first inner gas hole 134a when viewed in a direction parallel to the regulation surface of the guide portion 134b. FIG. 5 illustrates the positional relationship among the guide portions 134b and the sensor element 110 when the ratio R2/R1 is a value of 1. FIG. 6 illustrates the positional relationship between the guide portion 134b and the sensor element 110 when the ratio R2/R1 is a value of 2.38. Note that as illustrated in FIGS. 5 and 6, an angle θ5 formed by the regulation surface of the guide portion 134b and the external opening plane of the first inner gas hole 134a may be greater than or equal to 25° and less than or equal to 67.5°. In addition, the radius R2 may be greater than or equal to the width of the sensor element (i.e., the length of the sensor element in the right-left direction in FIG. 4) times 0.55 and less than or equal to the width times 1.30.

Each of the second inner gas holes 138a is formed so as to have a cross section that is perpendicular to the center axis of the second inner gas hole 138a is a true circle. In addition, the second inner gas hole 138a is formed so that a distance L between the center of the second inner gas hole 138a and the bottom surface of the inner protective cover 130 (refer to FIG. 2) is 3 mm or less. Such a range can further reliably prevent adhesion of water to the sensor element 110. In addition, as the distance L decreases, adhesion of water to the sensor element 110 can be more effectively prevented. Preferably, the distance L is 2.2 mm or less and, more preferably, the distance L is 1.1 mm or less. Furthermore, according to the present embodiment, a ratio A2/A1 defined by a ratio of an opening area A1 per first inner gas hole 134a and an opening area A2 per second inner gas hole 138a is higher than or equal to 0.9 and lower than or equal to 3.8. Thus, adhesion of water to the sensor element 110 can be sufficiently prevented. Preferably, the ratio A2/A1 is higher than or equal to 1.5 and lower than or equal to 1.9. Such a range can further effectively prevent adhesion of water to the sensor element 110. Note that the term "opening area of the second inner gas hole 138a" refers to an opening area of the second inner gas hole 138a when viewed in a direction of the flow of the gas to be measured that passes through the second inner gas hole 138a.

In addition, according to the present embodiment, for example, the diameter of the second inner gas hole 138a is in the range including, but not limited to, from 0.6 mm to 1.2 mm. According to the present embodiment, a ratio B2/B1 defined by a ratio of a total opening area B1 of the first inner gas holes 134a (the opening area per hole×the number of holes (i.e., 6)) to a total opening area B2 of the second inner gas holes 138a (the opening area per hole×the number of holes (i.e., 4)) is 0.85 or higher. Such a range can further reliably prevent adhesion of water to the sensor element 110. As the ratio B2/B1 increases, adhesion of water to the sensor element 110 can be more effectively prevented. Preferably, the ratio B2/B1 is 1.5 or higher. Note that the total opening area B2 may be greater than or equal to 1.55 mm$^2$ or may be greater than or equal to 2.8 mm$^2$.

Figure 7:
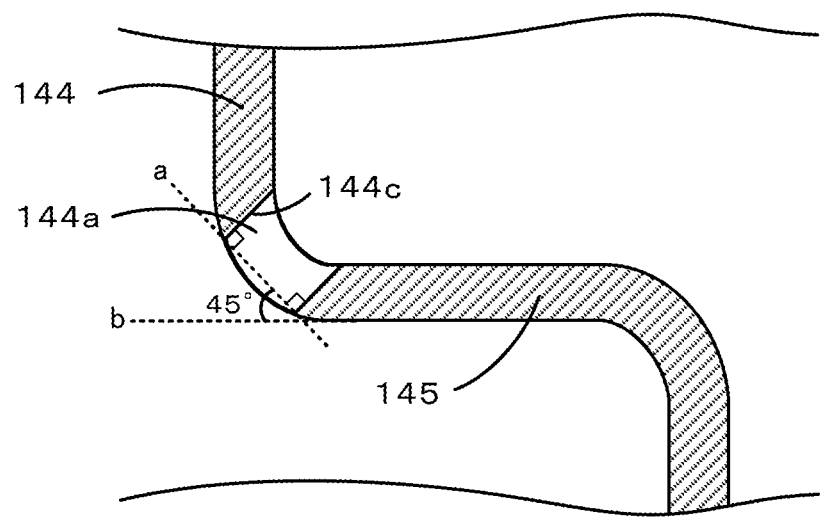
FIG. 7 is an enlarged partial cross-sectional view of a gas passing hole 144a and its vicinity illustrated in FIG. 2.
Figure 8:
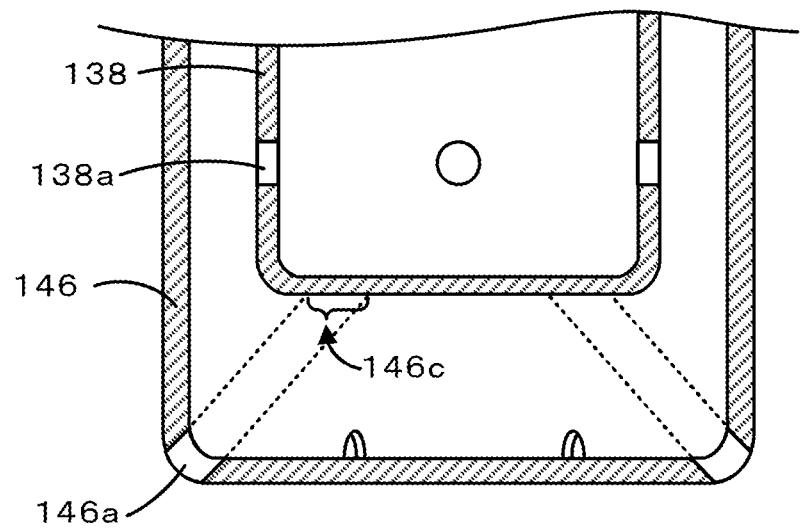
FIG. 8 is an enlarged partial cross-sectional view of an outer gas hole 146a and a second inner gas hole 138a and their vicinity illustrated in FIG. 2.

The outer protective cover 140 is formed from a metal member (e.g., a stainless steel member). The outer protective cover 140 includes a cylindrical large-diameter portion 142, a cylindrical body portion 144 that is connected to the large-diameter portion 142 and that has a diameter smaller than that of the large-diameter portion 142, and a bottomed cylindrical free end portion 146 having a diameter that is smaller than that of the body portion 144. In addition, the outer protective cover 140 includes a stepped portion 145 that connects the body portion 144 to the free end portion 146. Note that the center axes of the large-diameter portion 142, the body portion 144, and the free end portion 146 are the same as the center axis of the inner protective cover 130. The inner circumferential surface of the large-diameter portion 142 is in contact with the housing 102 and the large-diameter portion 132. Thus, the outer protective cover 140 is fixed to the housing 102. The body portion 144 is located so as to cover the outer circumferential surfaces of the first body portion 134 and the second body portion 136. The body portion 144 has six gas passing holes 144a formed therein at equal intervals. Each of the gas passing holes 144a allows the outside of the outer protective cover 140 to communicate with the first gas chamber 122. Each of the gas passing holes 144a is a circular hole and is located in a first corner portion 144b which is a boundary portion between the side surface of the body portion 144 and the bottom surface of the stepped portion 145. In addition, each of the gas passing holes 144a is formed so that the angle formed by the external opening plane of the gas passing hole 144a and the bottom surface of the stepped portion 145 is 45°, and the angle formed by the inner circumferential surface and the external opening plane of the gas passing hole 144a is 90°. Such a structure can further effectively prevent water from entering the outer protective cover 140 and adhering to the sensor element 110. In addition, the structure can reduce the flow velocity dependency of the responsiveness of the sensor element 110. FIG. 7 is an enlarged partial cross-sectional view of the gas passing hole 144a and its vicinity illustrated in FIG. 2. As illustrated in FIG. 7, the angle formed by the external opening plane of the gas passing hole 144a (a dashed line a) and the bottom surface of the stepped portion 145 (a dashed line b) is 45°. In addition, the angle formed by an inner circumferential surface 144c of the gas passing hole 144a and the external opening plane of the gas passing holes 144a (the dashed line a) is 90°. The free end portion 146 is located so as to cover the free end portion 138. The inner circumferential surface of the free end portion 146 is in contact with the outer circumferential surface of the second body portion 136. In addition, six outer gas holes 146a that allow the outside of the outer protective cover 140 to communicate with the second gas chamber 126 are formed in a second corner portion 146b which is a boundary portion between the side surface and the bottom surface of the free end portion 146 at equal intervals. Each of the outer gas holes 146a is a circular hole. Like the gas passing hole 144a, an angle θ1 formed by the external opening plane of the outer gas hole 146a and the bottom surface of the free end portion 146 is 45°. In addition, the angle formed by an inner circumferential surface and the external opening plane of the outer gas hole 146a is 90°. Such a structure can further effectively prevent water from entering the outer protective cover 140 and adhering to the sensor element 110. In addition, the structure can reduce the flow velocity dependency of the responsiveness of the sensor element 110. Furthermore, the positional relationship between the outer gas hole 146a and the second inner gas hole 138a is determined so that the second inner gas hole 138a is located in a region other than a region in an extension of the outer gas hole 146a. FIG. 8 is an enlarged partial cross-sectional view of the outer gas hole 146a and the second inner gas hole 138a and their vicinity illustrated in FIG. 2. As illustrated in FIG. 8, if imaginary directional light is emitted in a direction along the center axis of the outer gas hole 146a (a direction at an angle of 45° from the center axis direction of the outer protective cover 140), a region 146c that receives the light appears in the bottom surface of the free end portion 138 of the inner protective cover 130. The region 146c is referred to as a "region in an extension of the outer gas hole 146a". The second inner gas hole 138a is located in a region other than the region 146c. Note that the areas of the opening portions of the six gas passing holes 144a are the same, and the areas of the opening portions of the six outer gas holes 146a are the same. In addition, the area of the opening portion of one of the outer gas holes 146a is larger than the area of the opening portion of one of the gas passing holes 144a. Accordingly, since the number of the gas passing holes 144a is the same as the number of the outer gas holes 146a (i.e., 6), the total area of the outer gas holes 146a (the area per hole×the number of holes) is larger than the total area of the gas passing holes 144a. Note that each of the gas passing holes 144a and the outer gas holes 146a is formed so that the cross section that is perpendicular to the center axis thereof is a true circle. In addition, according to the present embodiment, for example, the diameter of the gas passing hole 144a is in the range including, but not limited to, from 0.8 mm to 1.2 mm. For example, the diameter of the outer gas hole 146a is in the range from 0.8 mm to 1.2 mm.

The first gas chamber 122 is formed from a space surrounded by the stepped portions 133 and 135, the first body portion 134, the second body portion 136, the large-diameter portion 142, the body portion 144, and the stepped portion 145. The sensor element chamber 124 is formed from a space surrounded by the inner protective cover 130. The second gas chamber 126 is formed from a space surrounded by the stepped portion 137, and the free end portions 138 and 146. Note that since the inner circumferential surface of the free end portion 146 is in contact with the outer circumferential surface of the second body portion 136, the first gas chamber 122 does not directly communicate with the second gas chamber 126.

The flow of the gas to be measured when the gas sensor 100 having such a configuration detects a predetermined gas concentration is described next. The gas to be measured flowing in the pipe 200 passes through any one of the gas passing holes 144a and enters the first gas chamber 122. Thereafter, the gas flows into the sensor element chamber 124 through any one of the first inner gas holes 134a. Subsequently, the gas to be measured flows from the sensor element chamber 124 into the second gas chamber 126 through any one of the second inner gas holes 138a and flows from the second gas chamber 126 to the outside through any one of the outer gas holes 146a.

Figure 9:
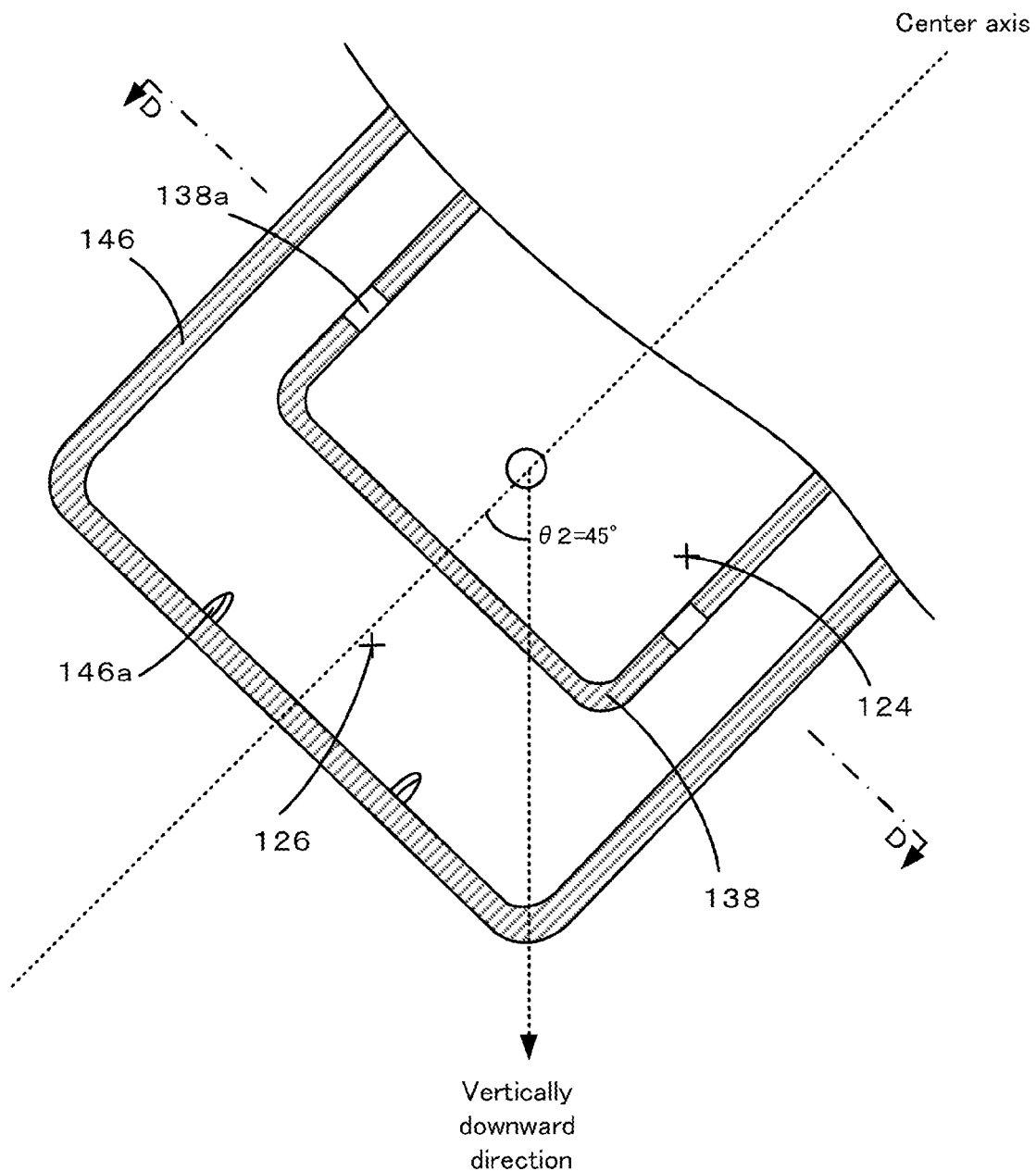
FIG. 9 is an enlarged partial cross-sectional view of the free end portion of the gas sensor 100 and its vicinity illustrated in FIG. 1B.
Figure 10:
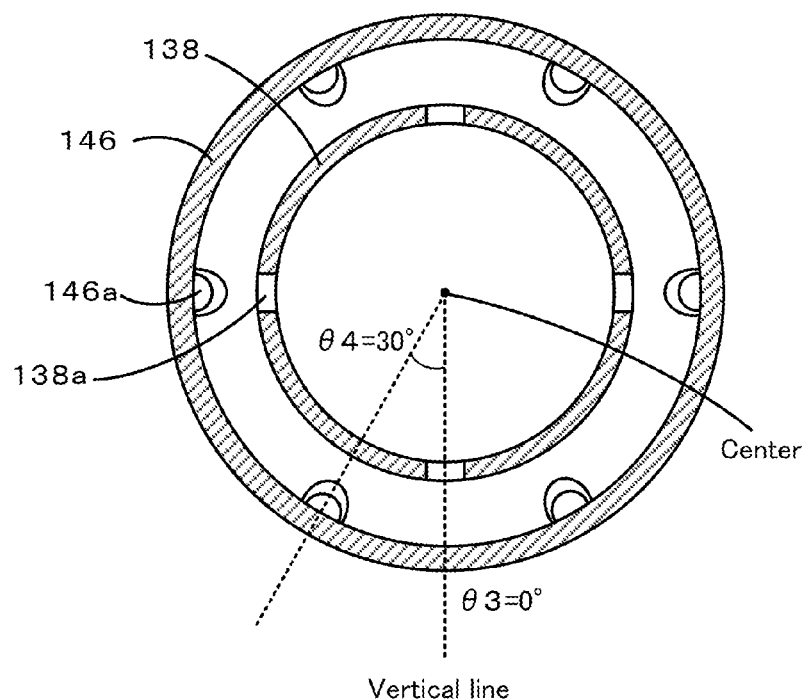
FIG. 10 is a cross-sectional view taken along a line D-D of FIG. 9.
Figure 11:
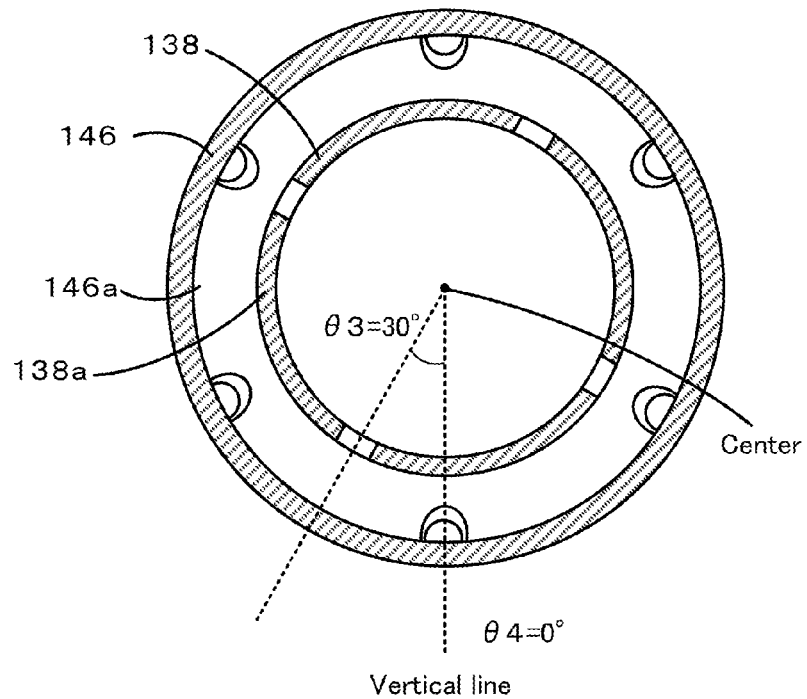
FIG. 11 is a cross-sectional view when a minimum value $\theta 3=30°$ and a minimum value $\theta 4=0°$.
Figure 12:
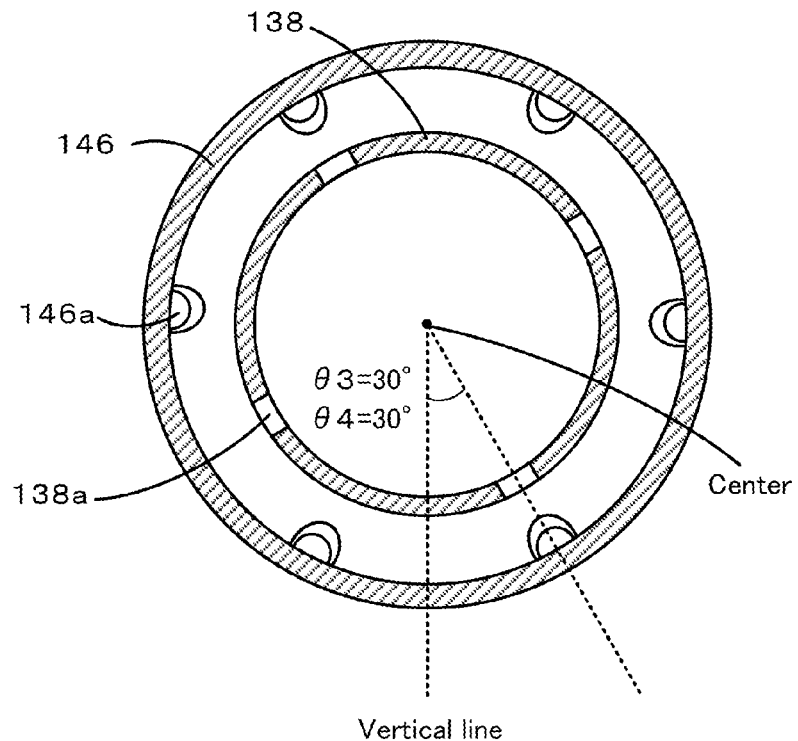
FIG. 12 is a cross-sectional view when the minimum value $\theta 3=30°$ and the minimum value $\theta 4=30°$.
Figure 13:
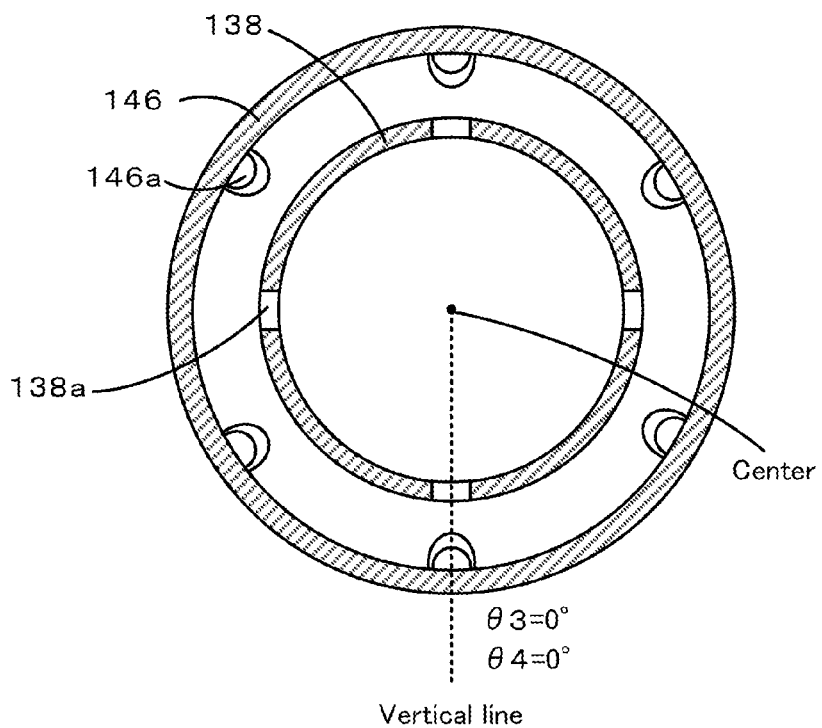
FIG. 13 is a cross-sectional view when the minimum value $\theta 3=0°$ and the minimum value $\theta 4=0°$.

A relationship among the second inner gas hole 138a, the outer gas hole 146a, and a vertically downward direction when the gas sensor 100 is attached to the pipe 200 is described next. FIG. 9 is an enlarged partial cross-sectional view of the free end portion of the gas sensor 100 and its vicinity illustrated in FIG. 1B. FIG. 10 is a cross-sectional view taken along a line D-D of FIG. 9. FIG. 10 is a cross-sectional view of the free end portions 138 and 146 cut by a plane perpendicular to the center axis of the inner protective cover 130. FIG. 10 also illustrates a vertical line obtained by projecting a line extending from the center of the inner protective cover 130 and the outer protective cover 140 in the vertically downward direction (refer to FIG. 9). According to the present embodiment, when, as illustrated in FIG. 10, the second inner gas hole 138a is projected onto a plane perpendicular to the center axis of the inner protective cover 130, a minimum value θ3 of the angle formed by a line extending between the center of the second inner gas hole 138a and the center of the inner protective cover 130 and the vertical line obtained by projecting a line extending from the center of the inner protective cover 130 in the vertically downward direction onto the plane is greater than or equal to 0° and is less than 45°. For example, in FIG. 10, an angle formed by a line extending between the center of the second inner gas hole 138a and the center of the inner protective cover 130 and the vertical line is obtained for each of the four second inner gas holes 138a. At that time, one hole having an angle of 0°, two holes having an angle of 90°, and one hole having an angle of 180° are found. Accordingly, the minimum value θ3 of the angles is 0°. As the minimum value θ3 is closer to 0°, the second inner gas hole 138a is located in the inner protective cover 130 closer to the vertically downward direction (the downward direction in FIG. 9). Therefore, water is easily drained from the second inner gas hole 138a. In this manner, adhesion of water to the sensor element 110 can be more effectively prevented. Note that it is more desirable that the minimum value θ3 be greater than or equal to 0° and less than or equal to 15°. Similarly, according to the present embodiment, when the outer gas hole 146a is projected onto a plane perpendicular to the center axis of the outer protective cover 140, a minimum value θ4 of the angle formed by a line extending between the center of the outer gas hole 146a and the center of the outer protective cover 140 and the vertical line obtained by projecting a line extending from the center of the outer protective cover 140 in the vertically downward direction onto the plane is greater than or equal to 0° and is less than or equal to 30°. For example, in FIG. 10, an angle formed by a line extending between the center of the outer gas hole 146a and the center of the outer protective cover 140 and the vertical line is obtained for each of the six outer gas holes 146a. At that time, two holes having an angle of 30°, two holes having an angle of 90°, and two holes having an angle of 150° are found. Accordingly, the minimum value θ4 of the angles is 30°. As the minimum value θ4 is closer to 0°, the outer gas hole 146a is located in the outer protective cover 140 so as to be closer to the vertically downward direction (the downward direction in FIG. 9). Therefore, water is easily drained from the outer gas hole 146a. In this manner, adhesion of water to the sensor element 110 can be more effectively prevented. FIG. 11 is a cross-sectional view when the minimum value θ3=30° and the minimum value θ4=0°. FIG. 12 is a cross-sectional view when the minimum value θ3=30° and the minimum value θ4=30°. FIG. 13 is a cross-sectional view when the minimum value θ3=0° and the minimum value θ4=0°. FIGS. 11, 12, and 13 correspond to figures illustrating the inner protective cover 130 and the outer protective cover 140 rotated from those of FIG. 10 by 30°, 60°, and 90° in a clockwise circumferential direction, respectively.

Figure 14:
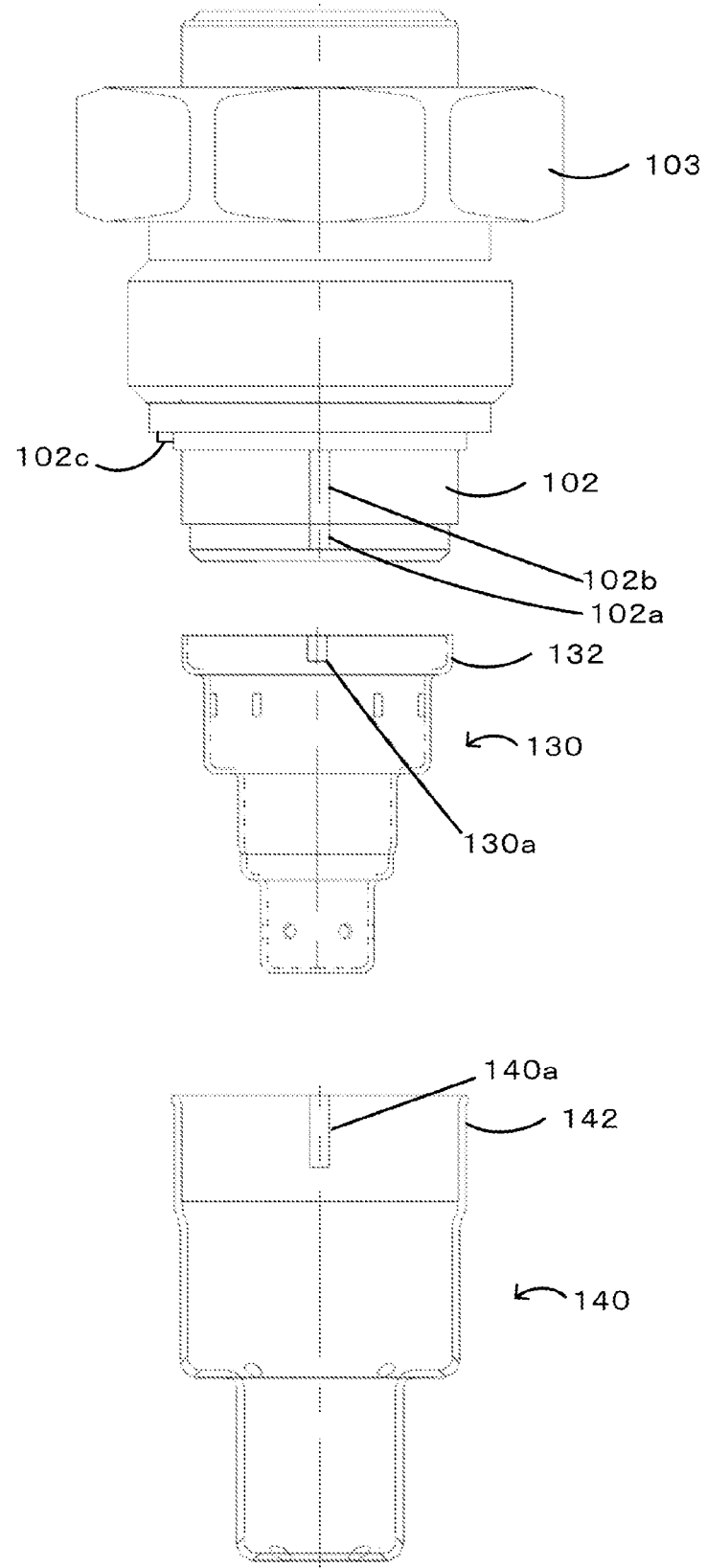
FIG. 14 is an exploded view illustrating a housing 102 with an inner protective cover 130 and an outer protective cover 140 removed.
Figure 15:
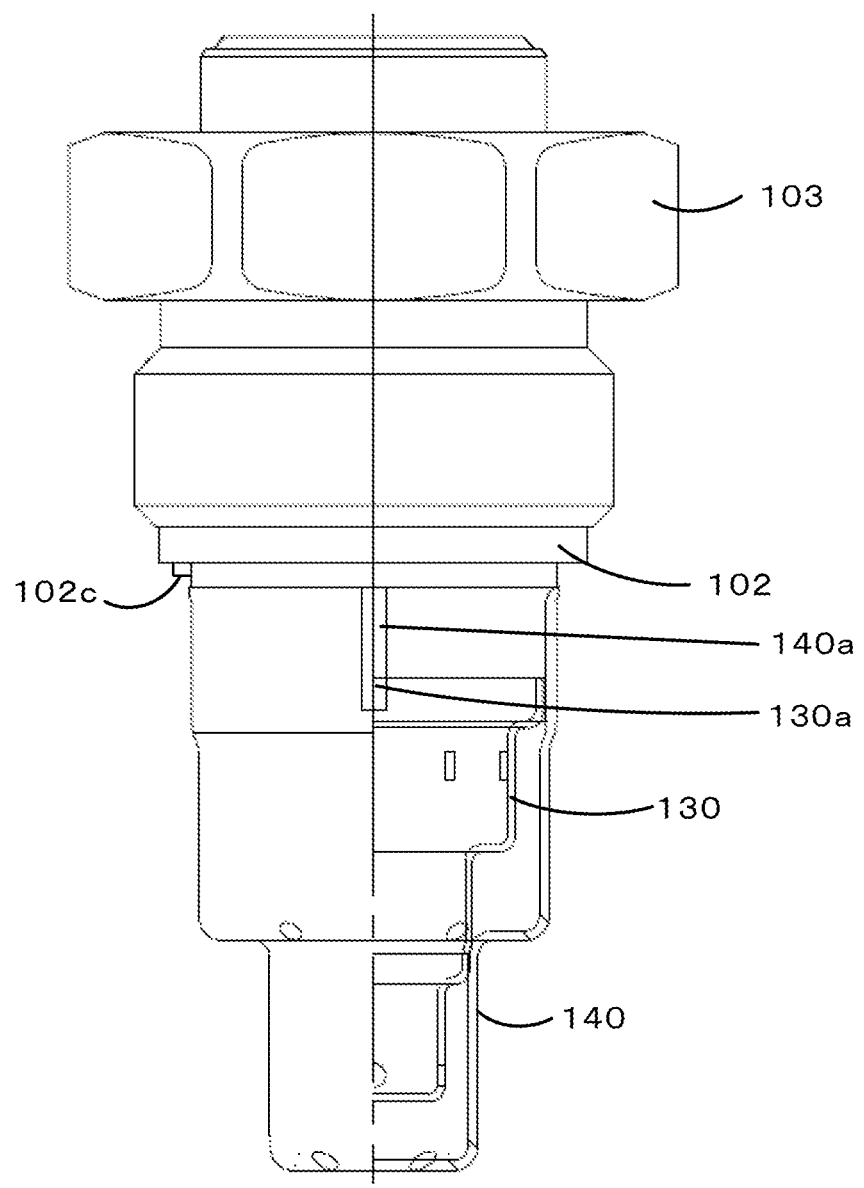
FIG. 15 illustrates a fracture cross-section of the housing 102 having the inner protective cover 130 and the outer protective cover 140 attached thereto.

A way of attaching the inner protective cover 130 and the outer protective cover 140 to the housing 102 is described next. FIG. 14 is an exploded view illustrating the housing 102 with the inner protective cover 130 and the outer protective cover 140 removed. FIG. 15 illustrates a fracture cross-section of the housing 102 having the inner protective cover 130 and the outer protective cover 140 attached thereto. Note that for convenience of description, in FIGS. 14 and 15, components other than the housing 102, the nut 103, the inner protective cover 130, and the outer protective cover 140 are not illustrated. As illustrated in the drawings, the housing 102 has convex portions 102a, 102b, and 102c formed on the outer circumferential surface thereof. In addition, the inner protective cover 130 has a concave portion 130a formed on the inner circumferential surface of the large-diameter portion 132, and the outer protective cover 140 has a concave portion 140a formed on the inner circumferential surface of the large-diameter portion 142. The convex portion 102a and the concave portion 130a form a pair of positioning portions. When the inner protective cover 130 is attached to the housing 102, the convex portion 102a is inserted into the concave portion 130a. Thus, the position at which the inner protective cover 130 is fixed to the housing 102 is determined. That is, if the inner protective cover 130 is rotated with respect to the housing 102 in the circumferential direction (if the concave portion 130a is offset from the convex portion 102a), the convex portion 102a interferes with the inner protective cover 130 and, therefore, the inner protective cover 130 cannot be attached. In this manner, control is performed so that the phase of the inner protective cover 130 relative to the housing 102 in the circumferential direction is always the same when the inner protective cover 130 is attached. Similarly, the convex portion 102b and the concave portion 140a form a pair of positioning portions. When the outer protective cover 140 is attached to the housing 102, the convex portion 102b is inserted into the concave portion 140a. Thus, the position at which the outer protective cover 140 is fixed to the housing 102 is determined. In this manner, control is performed so that the phase of the outer protective cover 140 relative to the housing 102 in the circumferential direction is always the same when the outer protective cover 140 is attached.

Figure 16A:
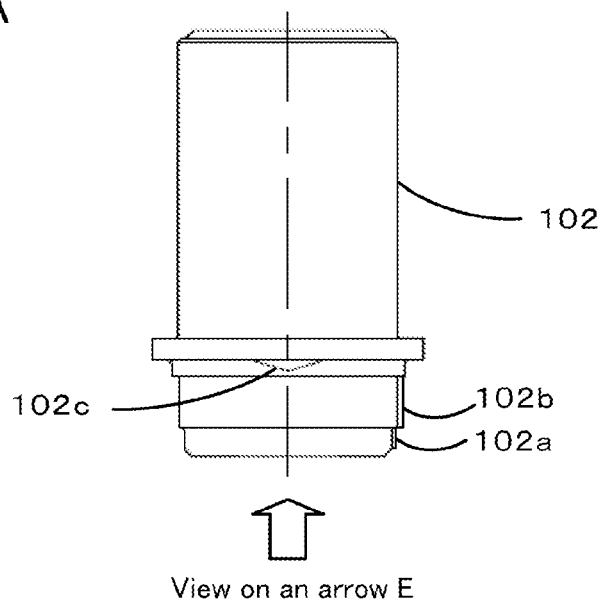
FIGS. 16A-16C illustrate only the housing 102 for convenience of description.
Figure 16B:
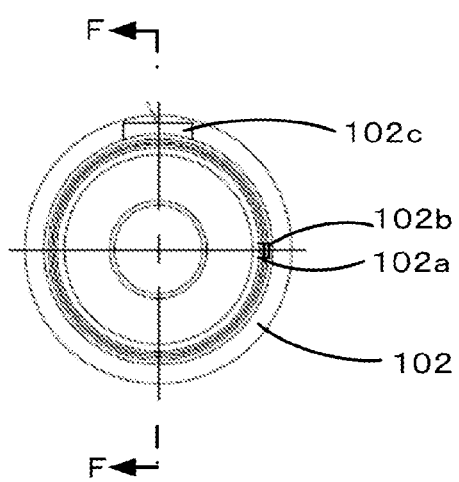
Figure 16C:
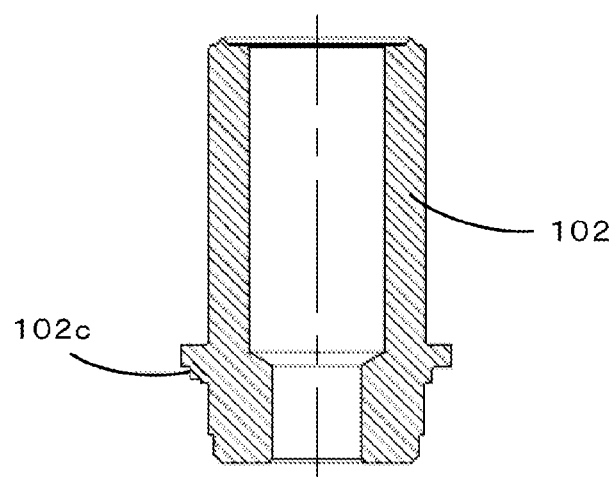
Figure 17A:
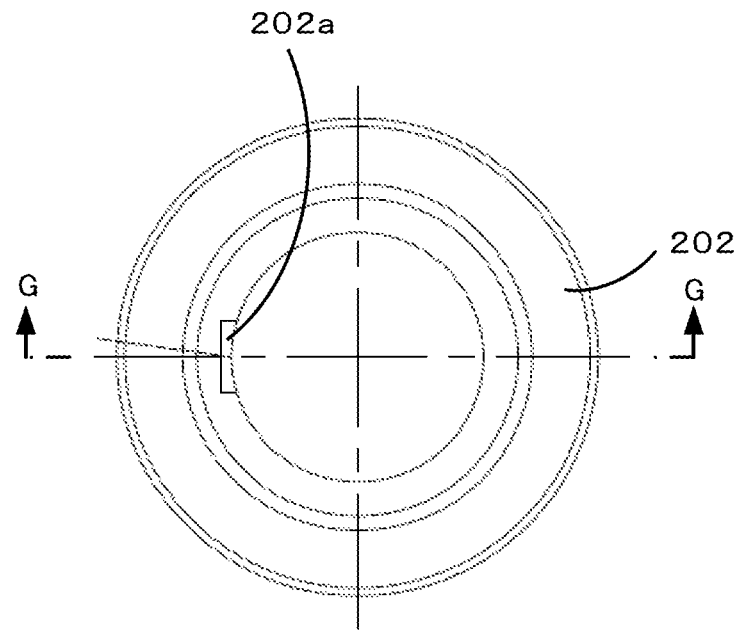
FIGS. 17A-17B illustrate only a fixing member 202 for convenience of description.
Figure 17B:
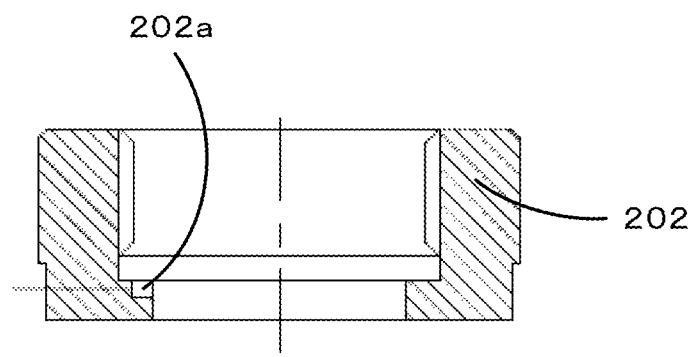
Figure 18:
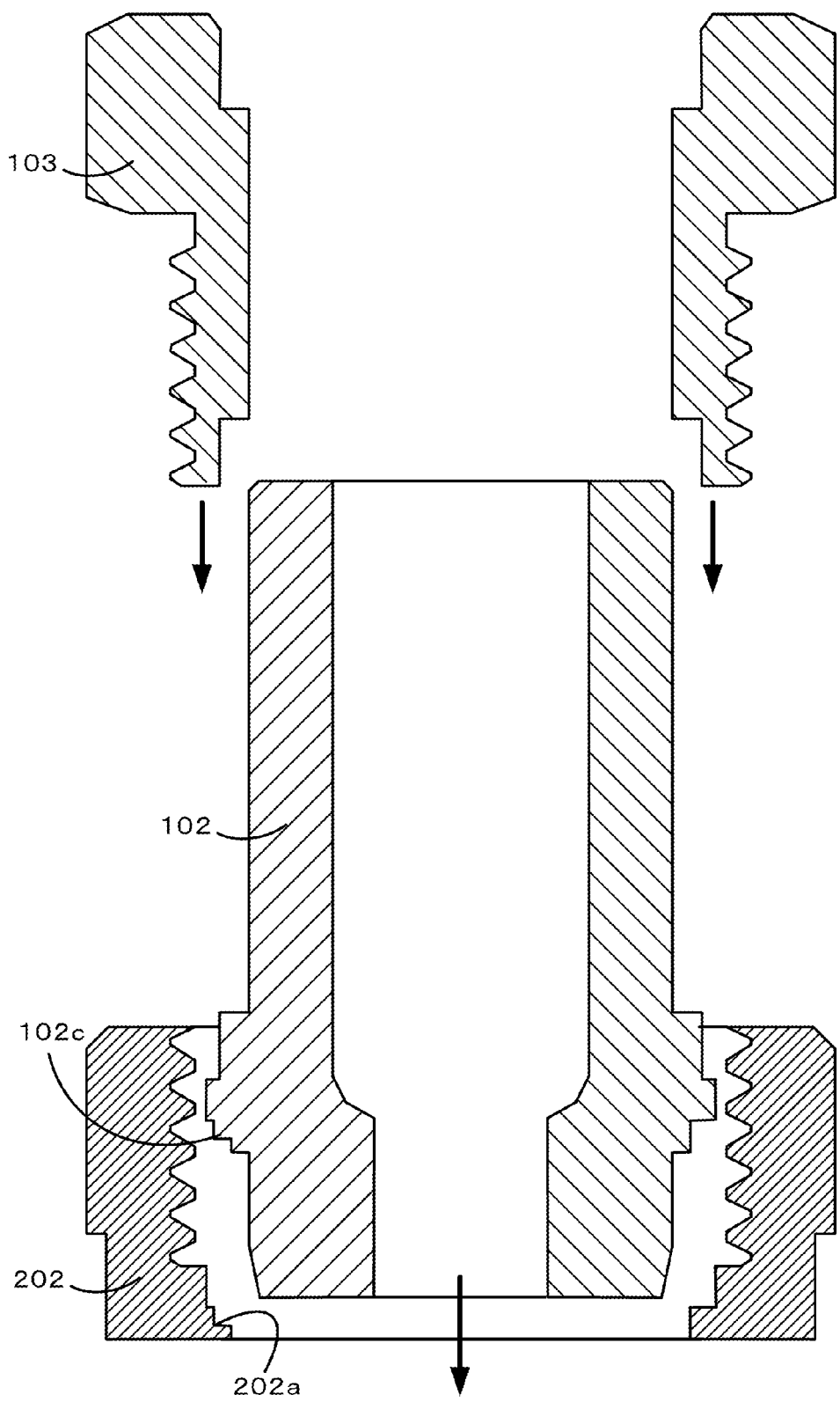
FIG. 18 illustrates an operation of attaching the housing 102 to the fixing member 202.

A way of attaching the housing 102 to the fixing member 202 is described next. For convenience of description, FIGS. 16A-16C illustrate only the housing 102. FIG. 16A is a side view of the housing 102, and FIG. 16B is a view on an arrow E of FIG. 16A. FIG. 16C is a cross-sectional view taken along a line F-F of FIG. 16B. For convenience of description, FIGS. 17A-17B illustrate only the fixing member 202. FIG. 17A is a top view of the fixing member 202, and FIG. 17B is a cross-sectional view taken along a line G-G of FIG. 17A. FIG. 18 illustrates an operation of attaching the housing 102 to the fixing member 202. For convenience of description, in FIG. 18, components other than the housing 102, the nut 103, and the fixing member 202 are not illustrated. As illustrated in the drawings, the housing 102 has the convex portion 102c on the outer circumferential surface thereof. In addition, the fixing member 202 has a concave portion 202a formed on the inner circumferential surface thereof. The convex portion 102c and the concave portion 202a form a pair of positioning portions. When the housing 102 is attached to the fixing member 202, the convex portion 102c is inserted into the concave portion 202a. Thus, the position at which the housing 102 is fixed to the fixing member 202 is determined. Accordingly, as illustrated in FIG. 18, the housing 102 is inserted into the fixing member 202 so that the concave portion 202a faces the convex portion 102c. In addition, the nut 103 is inserted into the fixing member 202 so that the housing 102 is attached. At that time, control is performed so that the phase of the housing 102 relative to the fixing member 202 in the circumferential direction is always the same when the housing 102 is attached.

As described above, according to the present embodiment, the housing 102 is fixed to the fixing member 202 in place, and the inner protective cover 130 and the outer protective cover 140 are fixed to the housing 102 in place. Accordingly, when the gas sensor 100 is attached to the pipe 200 via the fixing member 202, the positions at which the inner protective cover 130 and the outer protective cover 140 are fixed to the fixing member 202 are always the same. In addition, according to the present embodiment, the positions of the convex portions 102a, 102b, and 102c, the concave portions 130a, and the concave portions 140a and 202a are predetermined so that the above-described minimum value θ3 and minimum value θ4 are equal to predetermined values (e.g., the minimum value θ3=0°, and the minimum value θ4=30°) when the gas sensor 100 is attached to the pipe 200. Therefore, when the gas sensor 100 is attached to the pipe 200, by simply attaching the gas sensor 100 to the pipe 200 so that the convex portion 102a is inserted into the concave portion 130a, the convex portion 102b is inserted into the concave portion 140a, and the convex portion 102c is inserted into the concave portion 202a without measuring the minimum values θ3 and θ4 and positioning the second inner gas holes 138a and the outer gas holes 146a, the minimum value θ3 and the minimum value θ4 can be easily set to the predetermined values.

According to the present embodiment described in detail above, in the gas sensor 100, the ratio A2/A1 is set so as to be higher than or equal to 0.9 and lower than or equal to 3.8 and, more preferably, higher than or equal to 1.5 and lower than or equal to 1.9. Accordingly, adhesion of water to the sensor element 110 can be sufficiently prevented. In addition, the ratio B2/B1 is set so as to be higher than or equal to 0.85 and, more preferably, higher than or equal to 1.5. Accordingly, adhesion of water to the sensor element 110 can be more reliably prevented. Furthermore, since the distance L is set to shorter than or equal to 3 mm and, more preferably, shorter than or equal to 2.2 mm and, still more preferably, shorter than or equal to 1.1 mm, adhesion of water to the sensor element 110 can be more reliably effectively prevented. Furthermore, the outer gas hole 146a is formed in the boundary portion between the side surface and the bottom surface of the free end portion 146, and the formed angle θ1 is set to 45°. Accordingly, entry of water into the inner protective cover 130 and adhesion of water to the sensor element 110 can be more effectively prevented. In addition, the flow velocity dependency of the responsiveness of the sensor element 110 can be reduced. Still furthermore, since the ratio R2/R1 is greater than or equal to 1 and lower than or equal to 2.38, adhesion of water to the sensor element 110 and cooling of the sensor element 110 due to the flow of the gas to be measured can be more effectively prevented. Yet still furthermore, since the minimum value θ3 is greater than or equal to 0° and less than 45°, water can be easily drained from the second inner gas hole 138a. Thus, adhesion of water to the sensor element 110 can be more effectively prevented. Since the minimum value θ4 is greater than or equal to 0° and less than or equal to 30°, water can be easily drained from the outer gas hole 146a. Thus, adhesion of water to the sensor element 110 can be more effectively prevented. Yet still furthermore, by forming the convex portions 102a, 102b, and 102c, the concave portion 130a, and the concave portions 140a and 202a, the minimum value θ3 and the minimum value θ4 can be easily set to predetermined values.

It is apparent that the present invention is not limited to the above-described embodiment at all and various embodiments can be made within the technical scope of the present invention.

While the above embodiment has been described with reference to, for example, six first inner gas holes 134a and four second inner gas holes 138a, the numbers of the holes are not limited thereto. For example, any number of holes greater than or equal to one can be employed. In addition, the first inner gas holes 134a that are not located at equal intervals can be employed, and the second inner gas holes 138a that are not located at equal intervals can be employed. Furthermore, the first inner gas holes 134a can have different opening areas, and the second inner gas holes 138a can have different opening areas. Still furthermore, the shapes of the first inner gas hole 134a and the second inner gas hole 138a are not limited to those of the above-described embodiment.

While the above embodiment has been described with reference to six gas passing holes 144a and six outer gas holes 146a, the numbers of the gas passing holes 144a and the outer gas holes 146a are not limited thereto. For example, three or more gas passing holes 144a may be formed at equal intervals, and three or more outer gas holes 146a may be formed at equal intervals. Alternatively, two gas passing holes 144a and two outer gas holes 146a may be formed. Note that the gas passing holes 144a and the outer gas holes 146a may be formed at unequal intervals.

While the above embodiment has been described with reference to the angle formed by the external opening plane of the gas passing hole 144a and the bottom surface of the stepped portion 145 being 45°, the angle is not limited thereto. For example, the angle may be in the range from 10° to 80°. Even in such a case, if the gas passing hole 144a is located in the first corner portion 144b, water is easily drained from the gas passing hole 144a to the outside. Thus, adhesion of water to the sensor element 110 can be prevented. In addition, the flow velocity dependency of the responsiveness of the sensor element 110 can be reduced. Like the gas passing hole 144a, the angle θ1 formed by the external opening plane of the outer gas hole 146a and the bottom surface of the free end portion 146 is set to 45°. However, the angle θ1 may be in the range from 10° to 80°. Even in such a case, if the outer gas hole 146a is located in the second corner portion 146b, water is easily drained to the outside through the outer gas hole 146a. Thus, adhesion of water to the sensor element 110 can be prevented. In addition, the flow velocity dependency of the responsiveness of the sensor element 110 can be reduced.

Figure 19:
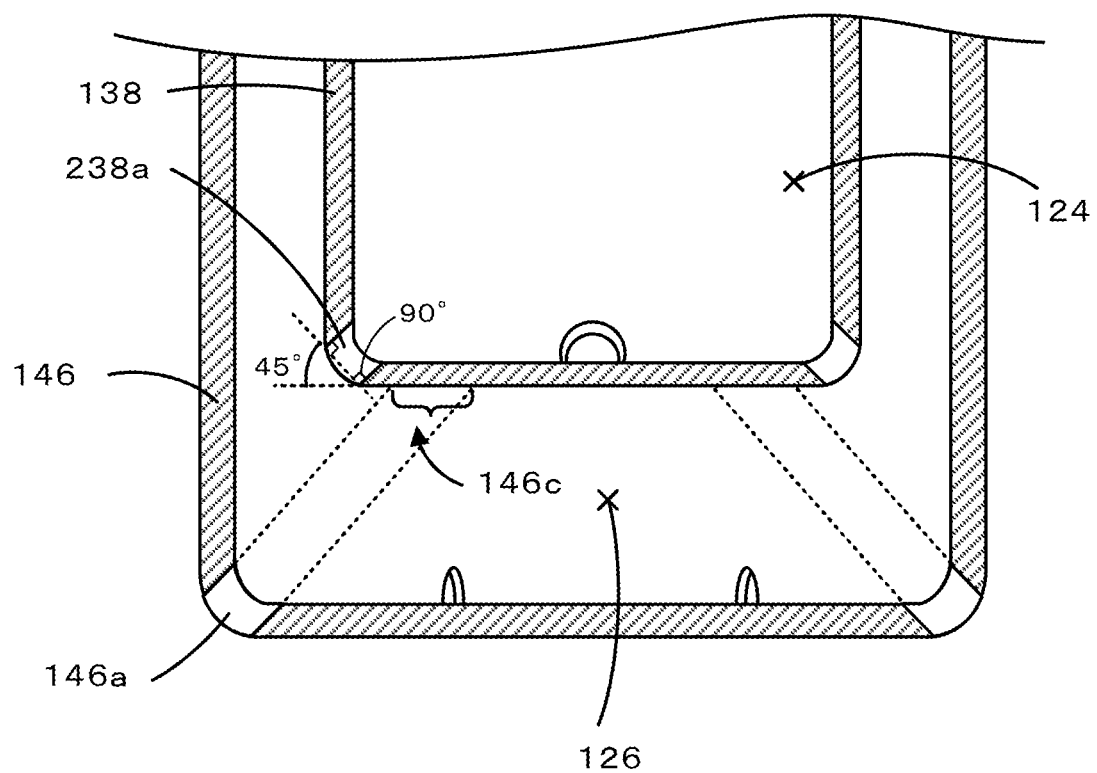
FIG. 19 is an enlarged partial cross-sectional view of a second inner gas hole 238a and its vicinity according to a modification.

While, as illustrated in FIG. 2, the above embodiment has been described with reference to the second inner gas hole 138a located in the side surface of the free end portion 138 of the inner protective cover 130, the location of the second inner gas hole 138a is not limited thereto. The second inner gas hole 138a may be located in a boundary portion between the side surface and the bottom surface of the inner protective cover. FIG. 19 is an enlarged partial cross-sectional view of the second inner gas hole and its vicinity when the second inner gas hole is located in a boundary portion between the side surface and the bottom surface of the inner protective cover. Note that in FIG. 19, the same numbering is used for the components as in FIG. 8 and, therefore, detailed description of the components is not provided. According to a modification, as illustrated in the drawing, unlike the second inner gas hole 138a illustrated in FIG. 8, a second inner gas hole 238a is formed so that the angle formed by the external opening plane of the second inner gas hole 238a and the bottom surface of the free end portion 138 of the inner protective cover 130 is 45°, and the angle formed by the inner circumferential surface and the external opening plane of the second inner gas hole 238a is 90°. Note that the angle formed by the external opening plane of the second inner gas hole 238a and the bottom surface of the free end portion 138 of the inner protective cover 130 is not limited to 45°. The angle may be in the range from 10° to 80°.

Figure 20:
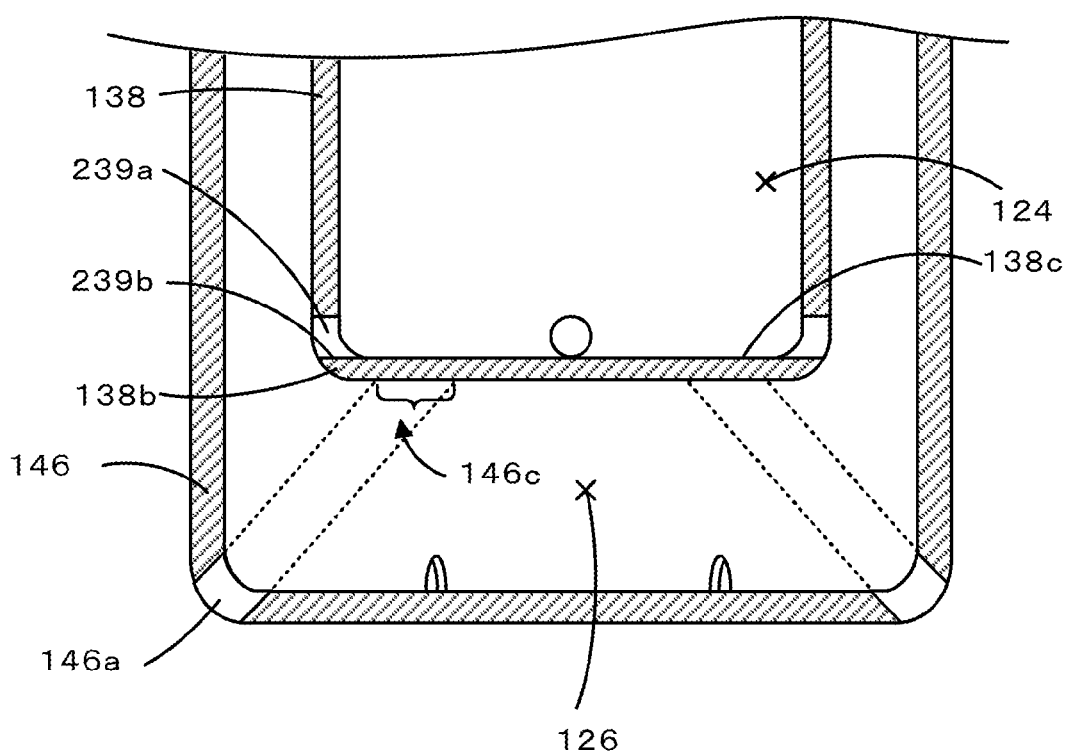
FIG. 20 is an enlarged partial cross-sectional view of a second inner gas hole 239a and its vicinity according to a modification.

While, as illustrated in FIG. 2, the above embodiment has been described with reference to the second inner gas hole 138a located in the middle portion of the side surface of the free end portion 138 of the inner protective cover 130, the location is not limited thereto. The second inner gas hole may be formed in the side surface of the free end portion 138 at a position close to the bottom surface or at a position close to the stepped portion 137. FIG. 20 is an enlarged partial cross-sectional view of the second inner gas hole and its vicinity when the second inner gas hole is disposed in the side surface of the free end portion 138 at a position close to the bottom surface. Note that in FIG. 20, the same numbering is used for the components as in FIG. 8 and, therefore, detailed description of the components is not provided. As illustrated in the drawing, according to a modification, a second inner gas hole 239a is disposed at a position spaced by a minimum distance from a corner portion 138b of the free end portion 138. In addition, the lowest surface 239b of the second inner gas hole 239a and an inner bottom surface 138c of the free end portion 138 are coplanar.

Figure 21:
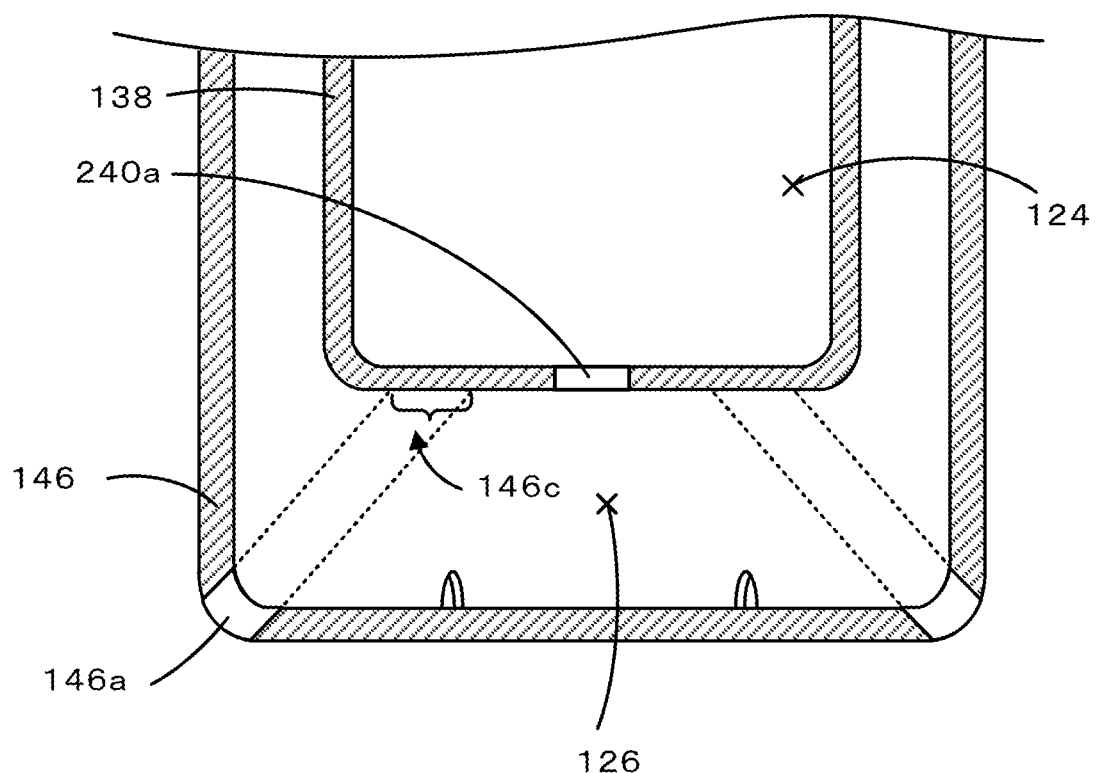
FIG. 21 is an enlarged partial cross-sectional view of a second inner gas hole 240a and its vicinity according to a modification.
Figure 22A:
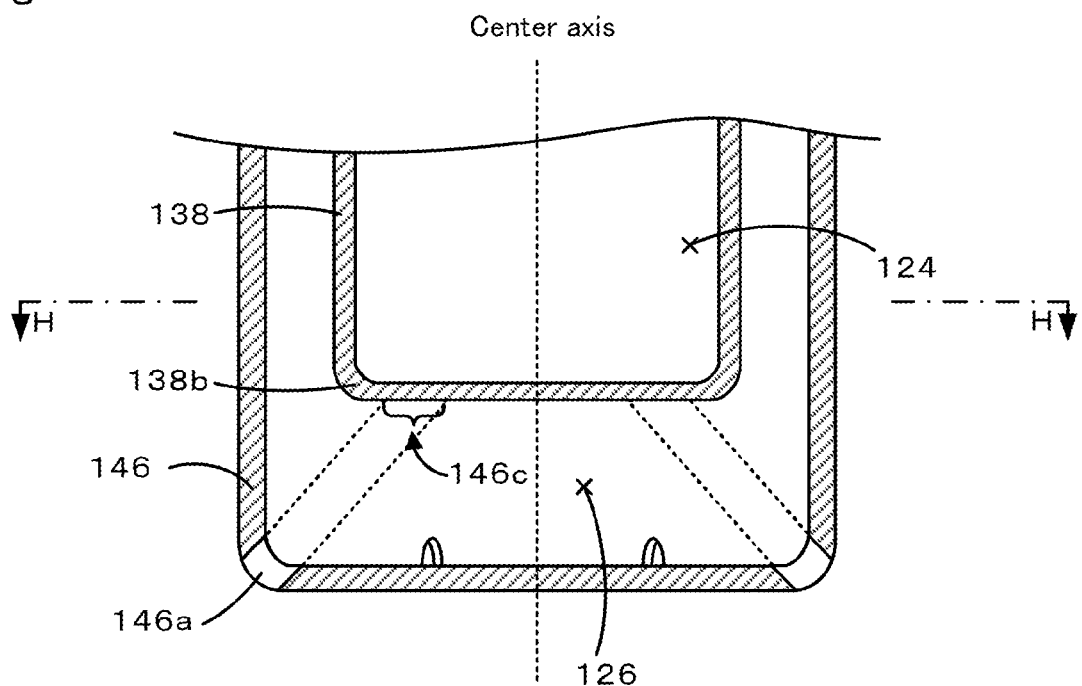
FIGS. 22A-22B illustrate a position of a second inner gas hole 241a according to a modification.
Figure 22B:
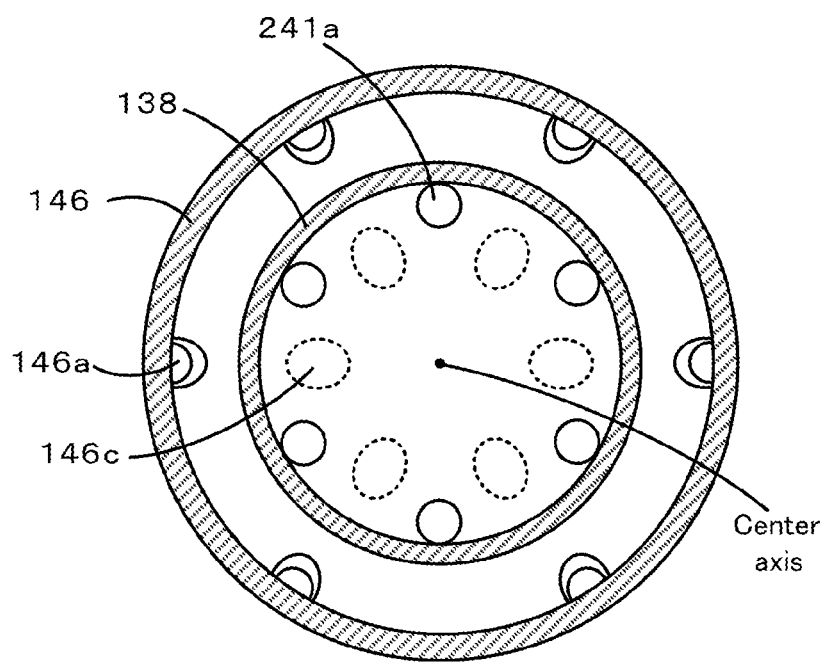

While, as illustrated in FIG. 2, the above embodiment has been described with reference to the second inner gas hole 138a located in the side surface of the free end portion 138 of the inner protective cover 130, the location is not limited thereto. The second inner gas hole 138a may be located in the bottom surface. FIG. 21 is an enlarged partial cross-sectional view of the second inner gas hole and its vicinity when the second inner gas hole is located in the bottom surface of the free end portion 138. Note that in FIG. 21, the same numbering is used for the components as in FIG. 8 and, therefore, detailed description of the components is not provided. As illustrated in the drawing, according to a modification, a second inner gas hole 240a is a circular hole located at the center of the bottom surface of the free end portion 138. Note that the second inner gas hole may be disposed at a location other than the center of the bottom surface of the free end portion 138. For example, the second inner gas hole may be disposed in the bottom surface of the free end portion 138 at a location spaced by a minimum distance from the corner of the free end portion 138. In such a case, the second inner gas hole may be disposed in a region other than the region 146c by offsetting the phase of the position of the second inner gas hole from the phase of the position of the region 146c in an extension of the outer gas holes 146a about the center axis of the free end portion 138 when viewed in the center axis direction of the free end portion 138 (the up-down direction in FIG. 2). FIGS. 22A-22B illustrate the position of the second inner gas hole in this case. FIG. 22A is a partial cross-sectional view of the free end portion 138 and its vicinity. FIG. 22B is a cross-sectional view taken along a line H-H of FIG. 22A. Note that in FIGS. 22A-22B, the same numbering is used for the components as in FIG. 8 and, therefore, detailed description of the components is not provided. As illustrated in FIG. 22B, according to a modification, six second inner gas holes 241a are formed at equal intervals at locations spaced by minimum distances from the corner portion 138b of the bottom surface of the free end portion 138. Accordingly, when viewed in the center axis direction as illustrated in FIG. 22B, the second inner gas hole 241a is located so as to be in contact with the inner circumferential surface of the side portion of the free end portion 138. In addition, when the center axis of the free end portion 138 is regarded as the central point, the second inner gas hole 241a is disposed so that the phase of the position of the second inner gas hole 241a is offset from the phase of the position of the region 146c. In this manner, the second inner gas hole 241a is located so as not to overlap the region 146c. Even when the second inner gas hole 241a is formed in this manner, water negligibly reaches the inside of the sensor element chamber 124 as in the present embodiment, since the second inner gas hole 241a is formed at a location outside the region 146c.

While the above embodiment has been described with reference to the second inner gas hole 138a, the gas passing hole 144a, and the outer gas hole 146a each having a cross section perpendicular to the center axis thereof being a true circle, the cross-sectional shape is not limited thereto. For example, the cross section perpendicular to the center axis may be elliptical or polygonal (e.g., rectangular).

While the above embodiment has been described with reference to the convex portion 102a and the concave portion 130a forming a pair of positioning portions, the convex portion 102b and the concave portion 140a forming a pair of positioning portions, and the convex portion 102c and the concave portion 202a forming a pair of positioning portions, the convex portion 102b and the concave portion 140a need not be formed. Even in such a case, the positional relationship among the fixing member 202, the housing 102, and the inner protective cover 130 can be controlled and, therefore, the minimum value θ3 can be easily set to a predetermined value. Similarly, the convex portion 102a and the concave portion 130a need not be formed. In addition, the concave portion and the convex portion may be exchanged. Furthermore, instead of the concave portion and the convex portion, a positioning portion having any shape that can control the positional relationship among the fixing member 202, the housing 102, the inner protective cover 130, and the outer protective cover 140 can be employed.

Figure 23:
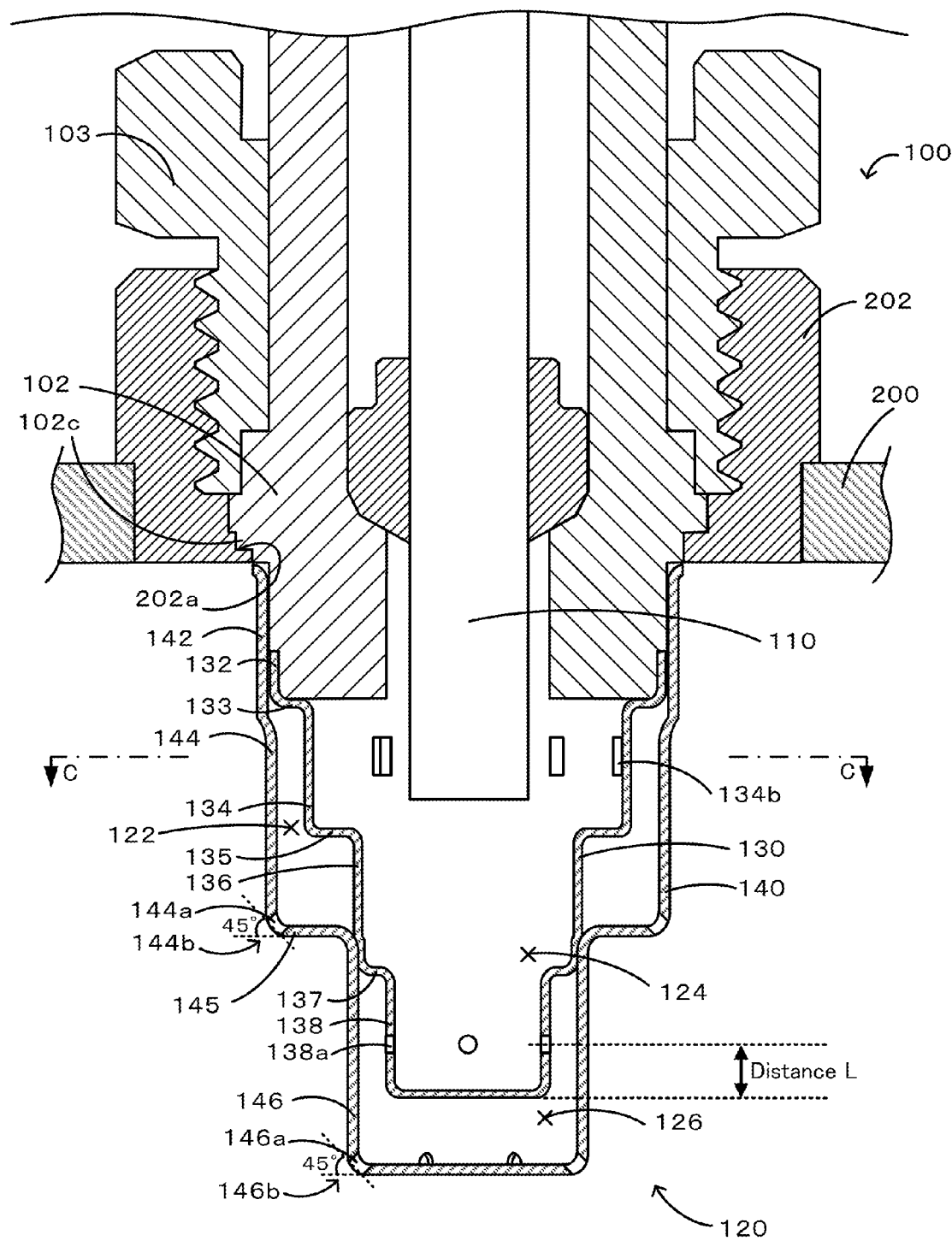
FIG. 23 is a cross-sectional view of a gas sensor 100 according to a modification.

While, as illustrated in FIG. 2, the above embodiment has been described with reference to the first body portion 134 and the second body portion 136 located so as to cover the side surface of the sensor element 110 and the free end of the sensor element 110 located in a space surrounded by the second body portion, the structure is not limited thereto. For example, as illustrated in FIG. 23, the sensor element 110 extending only up to a space surrounded by the first body portion 134 of the inner protective cover 130 may be employed. That is, the free end of the sensor element 110 may be located in a space surrounded by the first body portion 134. In this manner, the free end of the sensor element 110 is located closer to the first inner gas hole 134a than in the case illustrated in FIG. 2. Accordingly, the responsiveness of the sensor element 110 can be improved. In such a case, it is desirable that the free end of the sensor element 110 be located closer to the second inner gas hole 138a (the free end side of the inner protective cover 130) than the first inner gas hole 134a. Note that the sensor element 110 may reach a space surrounded by the free end portion 138 of the inner protective cover 130. That is, the free end of the sensor element 110 may be located in the space surrounded by the free end portion 138.

EXAMPLES

Experimental Example 1

The gas sensor 100 illustrated in FIG. 2 was produced. More specifically, the inner protective cover 130 had a thickness of 0.3 mm and an axis directional length of 17.7 mm. The large-diameter portion 132 had an axis directional length of 1.8 mm. The first body portion 134 had an axis directional length of 5.4 mm. The second body portion 136 had an axis directional length of 5.6 mm. The free end portion 138 had an axis directional length of 4.9 mm. The large-diameter portion 132 had an outer diameter of 14.1 mm. The first body portion 134 had an outer diameter of 11.8 mm. The second body portion 136 had an outer diameter of 8.2 mm. The free end portion 138 had an outer diameter of 5.9 mm. The opening area A1 per first inner gas hole 134a was 0.3053 mm$^2$. The number of the first inner gas holes 134a was 6. The value of the ratio R2/R1 was 4.35. The distance between the center of the first inner gas hole 134a and the free end of the inner protective cover 130 was 3.65 mm. Each of the second inner gas holes 138a had an inner diameter of 1.0 mm. The number of the second inner gas holes 138a was 4. The distance L was 1.1 mm. In addition, the outer protective cover 140 had a thickness of 0.4 mm and an axis directional length of 24.2 mm. The large-diameter portion 142 had an axis directional length of 6.1 mm. The body portion 144 had an axis directional length of 8.5 mm. The free end portion 146 had an axis directional length of 9.6 mm. The large-diameter portion 142 had an outer diameter of 15.2 mm. The body portion 144 had an outer diameter of 14.6 mm. The free end portion 146 had an outer diameter of 8.7 mm. Each of the gas passing holes 144a had an inner diameter of 1.0 mm. The number of the gas passing holes 144a was 6. The angle formed by the external opening plane of the gas passing hole 144a and the bottom surface of the stepped portion 145 was 45°. Each of the outer gas holes 146a had an inner diameter of 1.2 mm. The number of the outer gas holes 146a was 6. The angle θ1 formed by the outer gas hole 146a was 45°. Furthermore, the inner protective cover 130 and the outer protective cover 140 were attached to the housing 102 so that in a pipe, the minimum value θ3 was 0° and the minimum value θ4 was 30° (as illustrated in FIG. 10). The gas sensor 100 produced in this manner was used for the experimental example 1. Note that the first inner gas holes 134a were formed at equal intervals, the second inner gas holes 138a are formed at equal intervals, the gas passing holes 144a were formed at equal intervals, and the outer gas holes 146a were formed at equal intervals. Still furthermore, the sensor element 110 of the produced gas sensor 100 was used for detecting a concentration of oxygen.

Experimental Examples 2 to 16

The inner diameter of the second inner gas hole, the number of the second inner gas holes, the distance L, the minimum value θ3, and the minimum value θ4 were changed as indicated by "Experimental Examples 2 to 16" in Table 1. Note that the positional relationship among the second inner gas holes 138a and the outer gas holes 146a in experimental examples 3, 6, and 7 is the same as that illustrated in FIG. 13.

Figure 24:
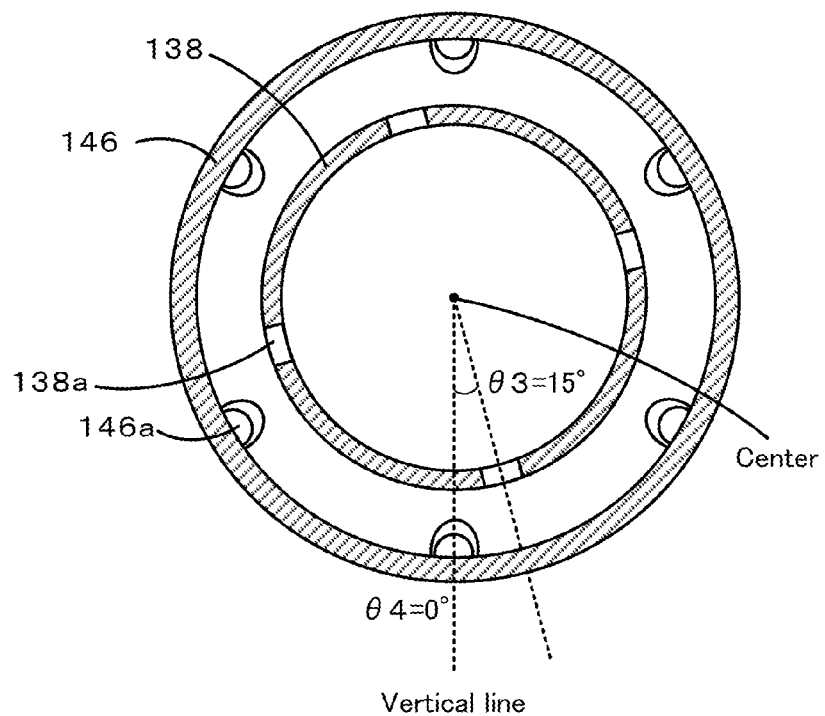
FIG. 24 is a cross-sectional view when a minimum value $\theta 3=15°$ and a minimum value $\theta 4=0°$
Figure 25:
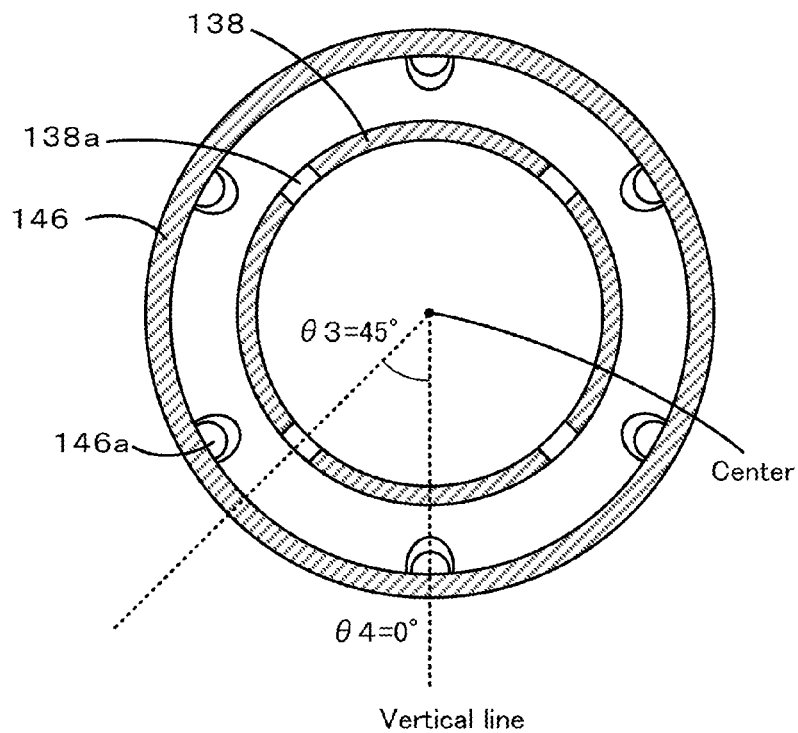
FIG. 25 is a cross-sectional view when the minimum value $\theta 3=45°$ and a minimum value $\theta 4=0°$
Figure 26:
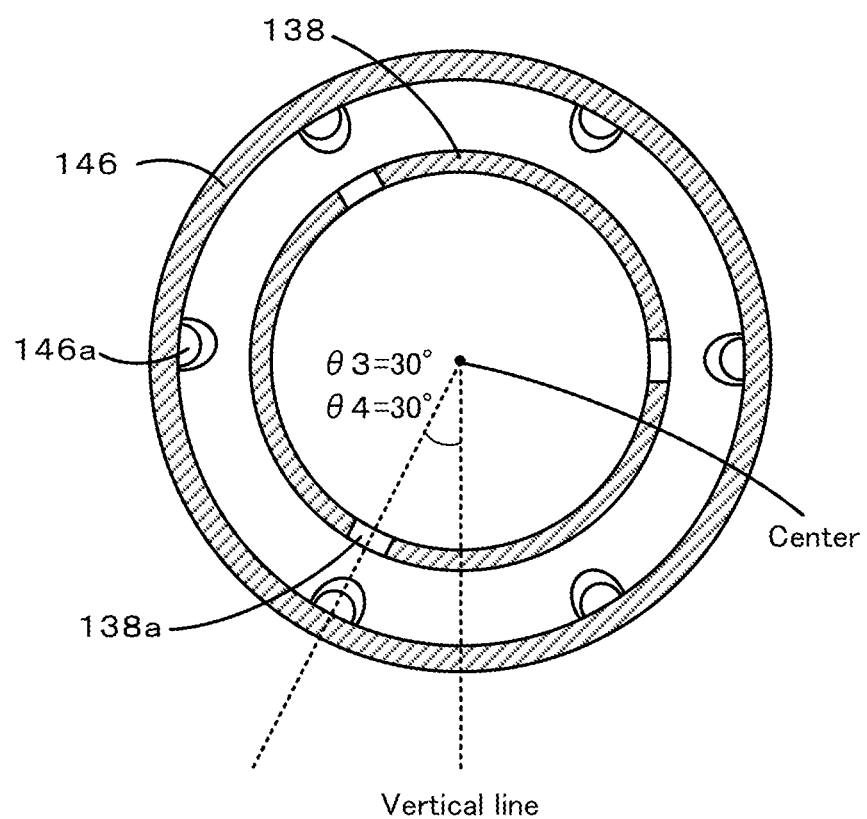
FIG. 26 is a cross-sectional view when the minimum value $\theta 3=30°$ and a minimum value $\theta 4=30°$.

The positional relationships among the second inner gas holes 138a and the outer gas holes 146a in experimental examples 4 and 5 are illustrated in FIGS. 24 and 25, respectively. The positional relationships among the second inner gas holes 138a and the outer gas holes 146a in experimental examples 2, 13 and 14 are illustrated in FIG. 26. In experimental examples 2 to 15, the second inner gas holes 138a were formed at equal intervals.

[Evaluation Test 1]

An amount of water remaining in the protective cover and a heater power control value were measured for each of the gas sensors 100. The measured values are illustrated in Table 1 and FIGS. 27 and 28. The amount of water remaining in the protective cover and the heater power control value were measured in the following manner.

Figure 29:
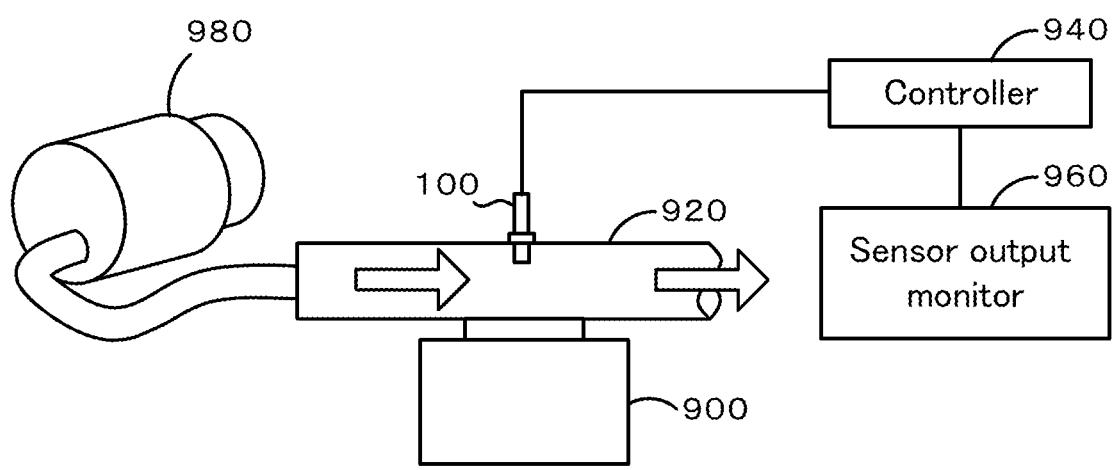
FIG. 29 illustrates how water drain tests are conducted.
Figure 29:
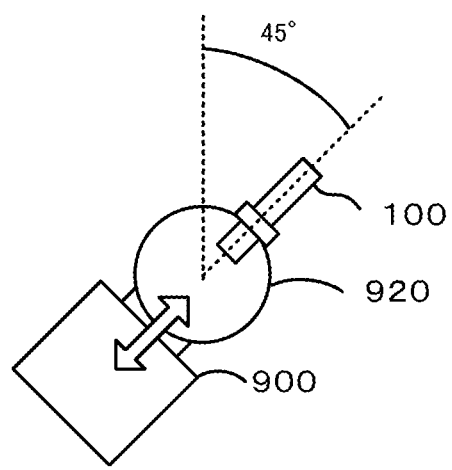

A water drain test was conducted. Drainage of water pre-contained in the inner protective cover was observed for each of the gas sensors 100 of experimental examples 1 to 16. FIG. 29 illustrates how the water drain tests were conducted. Note that the upper section of FIG. 29 shows the entire configuration for the water drain test, and the lower section of FIG. 29 is a partial cross-sectional view illustrating the inclination of the gas sensor 100 with respect to a pipe 920. This test was conducted in the following manner. The gas sensor was attached to the pipe 920 having a vibration exciter 900 mounted thereon along a direction at an angle of 45° to the vertical direction. In addition, a controller 940 that controls the output of a heater and a sensor output monitor 960 that measures the power control value of the heater were connected to the gas sensor 100. Subsequently, water of 0.1 g (0.1 cc) was poured into the inner protective cover 130, and the vibration exciter 900 vibrated the pipe 920 in the center axis direction of the gas sensor 100 with a sine wave by changing the frequency in the range from 10 to 200 Hz. At the same time, an air blower 980 was operated under a predetermined drive condition. Thus, air was sent from the air blower 980 to the pipe 920. During blasting, control was performed so that the temperature of the heater in the sensor element 110 was 100° C. At that time, the power control value of the heater was measured using the sensor output monitor 960. As the amount of water adhering to the sensor element 110 increases, the temperature of the sensor element 110 decreases. Thus, in order to increase the output of the heater, the heater power control value increases. In addition, the vibration was stopped at the same time as the operation of the air blower 980 was completed. Then, a total of water remaining inside the outer protective cover 140 and the inner protective cover 130 was measured as the amount of remaining water. Note that the predetermined drive condition for the air blower 980 was a condition in which an air flow of about 75 m/s was generated by an air blower and was sent to the pipe 920 for 3 seconds. Furthermore, in experimental examples 3 to 7, only the amount of remaining water was measured.

TABLE 1

| Experimental example | First inner gas hole Area A1 (mm$^2$) | First inner gas hole Number of holes | Second inner gas hole Inner diameter (mm) | Second inner gas hole Number of holes | Area ratio A2/A1 | Total area ratio B2/B1 | Distance L (mm) | Ratio R2/R1 | Angle θ1 (°) | Minimum value θ3 (°) | Minimum value θ4 (°) | Amount of remaining water (g) | Heater power control value |
|---|---|---|---|---|---|---|---|---|---|---|---|---|---|
| 1 | 0.3053 | 6 | 1.0 | 4 | 2.5730 | 1.7153 | 1.1 | 4.35 | 45 | 0 | 30 | 0.004 | 1.29 |
| 2 | 0.3053 | 6 | 1.2 | 3 | 3.7051 | 1.8525 | 1.2 | 4.35 | 45 | 30 | 30 | 0.060 | 1.38 |
| 3 | 0.3053 | 6 | 1.0 | 4 | 2.5730 | 1.7153 | 1.1 | 4.35 | 45 | 0 | 0 | 0.001 | — |
| 4 | 0.3053 | 6 | 1.0 | 4 | 2.5730 | 1.7153 | 1.1 | 4.35 | 45 | 15 | 0 | 0.012 | — |

TABLE 1-continued

| Experimental example | First inner gas hole | | Second inner gas hole | | Area ratio A2/A1 | Total area ratio B2/B1 | Distance L (mm) | Ratio R2/R1 | Angle θ1 (°) | Minimum value θ3 (°) | Minimum value θ4 (°) | Amount of remaining water (g) | Heater power control value |
|---|---|---|---|---|---|---|---|---|---|---|---|---|---|
| | Area A1 (mm²) | Number of holes | Inner diameter (mm) | Number of holes | | | | | | | | | |
| 5 | 0.3053 | 6 | 1.0 | 4 | 2.5730 | 1.7153 | 1.1 | 4.35 | 45 | 45 | 0 | 0.018 | — |
| 6 | 0.3053 | 6 | 1.0 | 4 | 2.5730 | 1.7153 | 3.0 | 4.35 | 45 | 0 | 0 | 0.040 | — |
| 7 | 0.3053 | 6 | 1.0 | 4 | 2.5730 | 1.7153 | 3.5 | 4.35 | 45 | 0 | 0 | 0.065 | — |
| 8 | 0.3053 | 6 | 0.8 | 6 | 1.6467 | 1.6467 | 2.2 | 4.35 | 45 | 30 | 30 | 0.013 | 1.38 |
| 9 | 0.3053 | 6 | 0.8 | 6 | 1.6467 | 1.6467 | 1.1 | 4.35 | 45 | 30 | 30 | 0.001 | 1.48 |
| 10 | 0.3053 | 6 | 0.6 | 10 | 0.9263 | 1.5438 | 2.2 | 4.35 | 45 | 18 | 30 | 0.027 | 1.42 |
| 11 | 0.3053 | 6 | 0.4 | 12 | 0.4117 | 0.8233 | 1.1 | 4.35 | 45 | 0 | 30 | 0.097 | 1.00 |
| 12 | 0.3053 | 6 | 0.6 | 6 | 0.9263 | 0.9263 | 1.1 | 4.35 | 45 | 30 | 30 | 0.076 | 1.38 |
| 13 | 0.3053 | 6 | 0.8 | 3 | 1.6467 | 0.8233 | 1.1 | 4.35 | 45 | 30 | 30 | 0.051 | 1.21 |
| 14 | 0.3053 | 6 | 0.8 | 3 | 1.6467 | 0.8233 | 2.2 | 4.35 | 45 | 30 | 30 | 0.088 | 1.27 |
| 15 | 0.3053 | 6 | 1.0 | 2 | 2.5730 | 0.8577 | 1.1 | 4.35 | 45 | 90 | 30 | 0.055 | 1.40 |
| 16 | 0.3053 | 6 | 1.4 | 1 | 5.0430 | 0.8405 | 1.1 | 4.35 | 45 | 90 | 30 | 0.080 | 1.85 |

Figure 27:
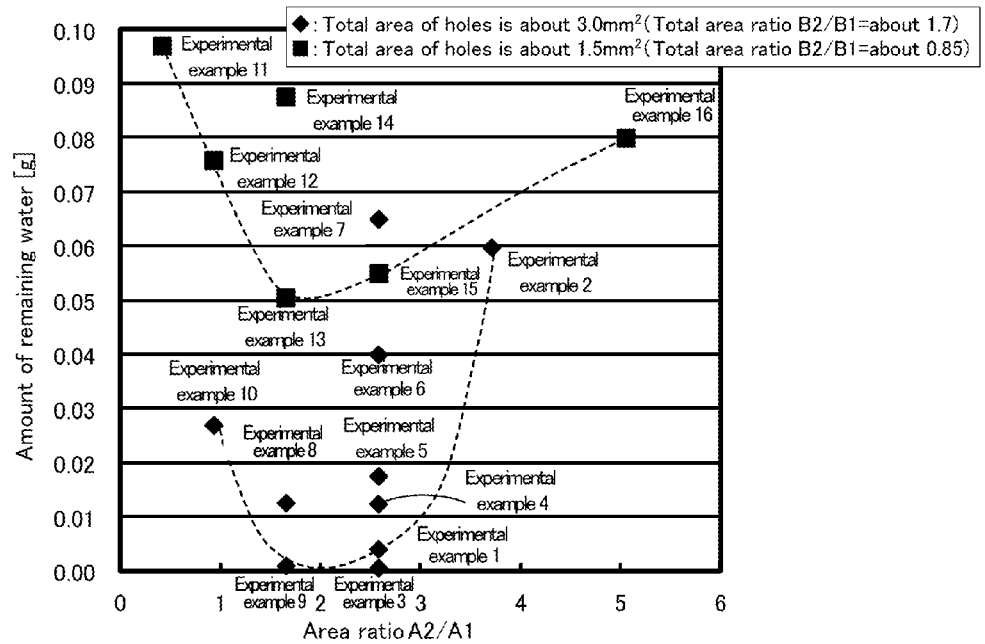
FIG. 27 is a graph illustrating a relationship between an area ratio A2/A1 and an amount of remaining water.
Figure 28:
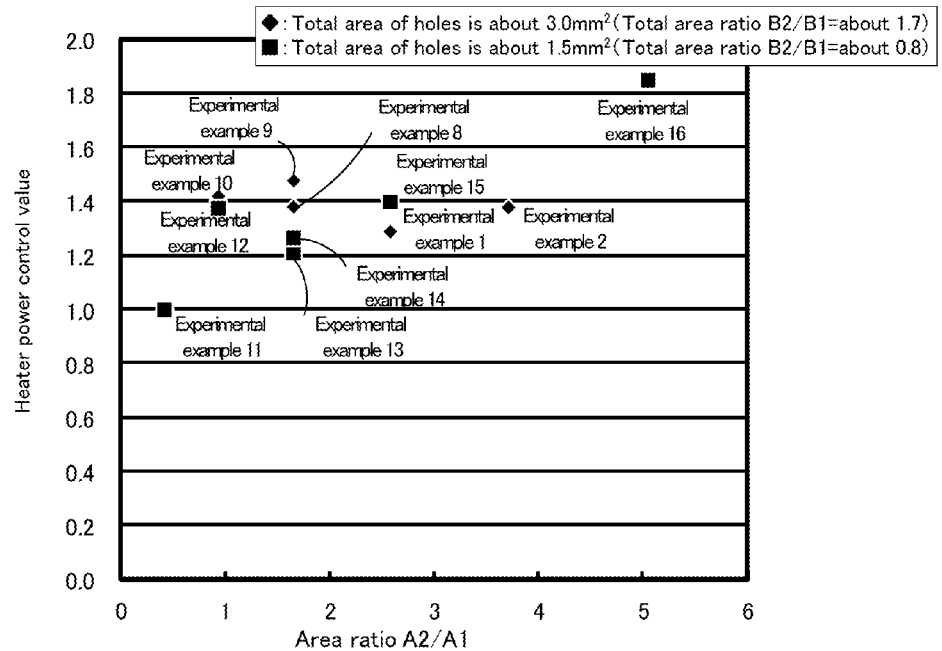
FIG. 28 is a graph illustrating a relationship between an area ratio A2/A1 and a heater power control value.

FIG. 27 is a graph illustrating a relationship between an area ratio A2/A1 and the amount of remaining water. FIG. 28 is a graph illustrating a relationship between the area ratio A2/A1 and the heater power control value. As can be seen from Table 1 and FIG. 27, in experimental examples 1 to 10 and experimental examples 12 to 15 in which the area ratio A2/A1 is higher than or equal to 0.9 and lower than or equal to 3.8, the amount of remaining water is smaller than that in experimental example 11 in which the area ratio A2/A1 is lower than 0.9. In addition, in experimental examples 1 to 10 and experimental examples 12, 13, and 15, the amount of remaining water is smaller than that in experimental example 16 in which the area ratio A2/A1 is higher than 3.8. In addition, a comparison of experimental examples 1, 2, 9, and 10 in which conditions other than the area ratio A2/A1 (e.g., the distance L) indicates that the amount of remaining water in experimental example 9 in which the area ratio A2/A1 is higher than or equal to 1.5 and lower than or equal to 1.9 is in particular small. Furthermore, in experimental examples 1 to 10 and experimental examples 12 and 15 in which the ratio B2/B1 is higher than or equal to 0.85, the amount of remaining water is smaller than those in experimental examples 11 and 16 in which the total area ratio B2/B1 is lower than 0.85. Still furthermore, in experimental examples 1 to 10 in which the total area ratio B2/B1 is about 1.7 (higher than or equal to 1.5), the amount of remaining water is generally smaller than those in experimental examples 11 to 16 in which the total area ratio B2/B1 is about 0.8. Yet still furthermore, a comparison of experimental examples 3, 6, and 7 in which only the distances L differ from one another indicates that the amount of remaining water in experimental examples 3 and 6 in which the distance L is less than or equal to 3 mm is smaller than that in experimental example 7 in which the distance L is greater than 3 mm and, in particular, the amount of remaining water in experimental example 3 in which the distance L is less than or equal to 1.1 mm is small. Yet still furthermore, a comparison of experimental examples 6 and 8 in which conditions other than the distances L are relatively close to each other indicates that the amount of remaining water in experimental example 8 in which the distance L is less than or equal to 2.2 mm is smaller than that in experimental example 6. A comparison of experimental examples 13 and 14 in which conditions other than the distances L are the same indicates that the amount of remaining water in experimental example 13 in which the distance L is less than or equal to 1.1 mm is smaller than that in experimental example 14. Yet still furthermore, a comparison of experimental examples 3 to 5 in which the minimum values θ3 differ from one another indicates that the amount of remaining water in experimental examples 3 and 4 in which the minimum value θ3 is less than 45° is smaller than that in experimental example 5 in which the minimum value θ3 is 45°. In particular, the amount of remaining water in experimental example 3 in which the minimum value θ3 is 0° is small. As can be seen from Table 1 and FIG. 28, the amount of remaining water in each of experimental examples 1 to 10 and experimental examples 12, 13, and 15 is smaller than those in experimental examples 11 and 16. In addition, the heater power control value in each of experimental examples 1 to 10 and experimental examples 12, 13, and 15 is smaller than that in experimental example 16. Furthermore, the increase ratio of the heater power control value in each of experimental examples 1 to 10 and experimental examples 12 to 15 to that in experimental example 11 is relatively smaller than the decrease ratio of the amount of remaining water in each of experimental examples 1 to 10 and experimental examples 12 to 15 to that in experimental example 11.

Experimental Examples 17 to 20

Figure 30:
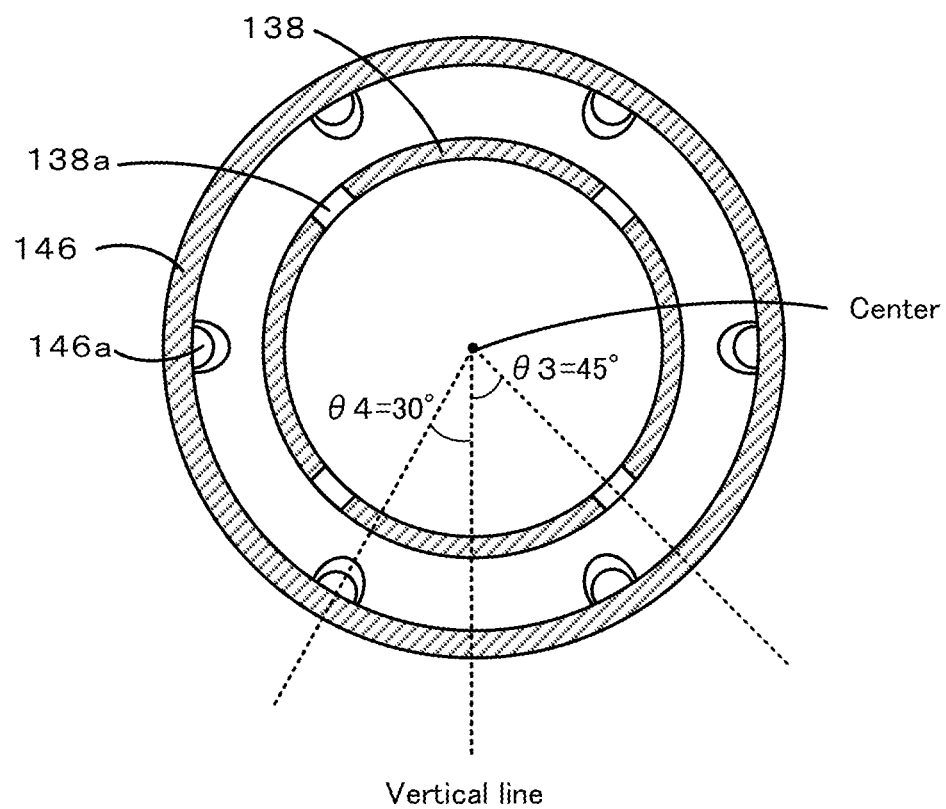
FIG. 30 is a cross-sectional view when the minimum value $\theta 3=45°$ and a minimum value $\theta 4=30°$.

By using the gas sensor of experimental example 1 as a reference, only the inner protective cover was rotated by a rotation angle indicated by Table 2 so that the phase was changed. In this manner, the minimum value θ3 was changed as indicated by Table 2. Thus, gas sensors of experimental examples 17 to 20 were produced. Note that the positional relationship among the second inner gas holes 138a and the outer gas holes 146a in each of experimental examples 17 and 19 is the same as that illustrated in FIG. 12. FIG. 30 illustrates the positional relationship among the second inner gas holes 138a and the outer gas holes 146a in experimental example 18. Although the rotation angles in experimental examples 17 and 19 with respect to the angle in experimental example 1 differ from each other (30° and 60°, respectively), the positional relationships among the second inner gas holes 138a and the outer gas holes 146a are practically the same. Similarly, the positional relationship in experimental examples 1 and 20 are practically the same.

Experimental Examples 21 to 26

By using the gas sensor of experimental example 3 as a reference, only the inner protective cover was rotated by a rotation angle indicated by Table 2 so that the phase was changed. In this manner, the minimum value θ3 was changed as indicated by Table 2. Thus, gas sensors of experimental examples 21 to 26 were produced. The positional relationship among the second inner gas holes 138a and the outer gas holes 146a in each of experimental examples 22 and 24 is the same as that illustrated in FIG. 11. Note that each of experimental examples 21 and 25 is practically the same as experimental example 4. Experimental example 22 is practically the same as experimental example 24. Experimental example 23 is practically the same as experimental example 5. Experimental example 26 is practically the same as experimental example 3.

reference gas to when the sensor output rose to 10% of the maximum value at the rise time and a time period t90 from when the oxygen was introduced into the reference gas to when the sensor output rose to 90% of the maximum value at the rise time were obtained. Subsequently, a difference Δt (=t90−t10) was defined as a response time (sec). As the response time decreases, the responsiveness of the gas sensor increases. Note that the test was conducted using the pipe 200 having a diameter of 28 mm for the gas sensors of experimental example 1, experimental examples 17 to 20, experimental example 3, experimental examples 22 to 24, and experimental example 26. In addition, the test was conducted using the pipe 200 having a diameter of 55 mm for the gas sensors of experimental examples 1, 18, 20, 3, 23, and 26.

TABLE 2

| Experimental example | First inner gas hole | | Second inner gas hole | | Total Area ratio A2/A1 | Distance area ratio B2/B1 | L (mm) | Ratio R2/R1 | Angle θ1 (°) | Minimum value θ3 (°) | Minimum value θ4 (°) | Inner cover Rotation angle (°) | Amount of remaining water (g) | Response time(sec) | |
|---|---|---|---|---|---|---|---|---|---|---|---|---|---|---|---|
| | Area A1 (mm²) | Number of holes | Inner diameter (mm) | Number of holes | | | | | | | | | | Diameter of pipe 28 mm | Diameter of pipe 55 mm |
| 1 | 0.3053 | 6 | 1.0 | 4 | 2.5730 | 1.7153 | 1.1 | 4.35 | 45 | 0 | 30 | 0(reference) | 0.004 | 0.67 | 0.92 |
| 17 | 0.3053 | 6 | 1.0 | 4 | 2.5730 | 1.7153 | 1.1 | 4.35 | 45 | 30 | 30 | 30 | — | 0.66 | — |
| 18 | 0.3053 | 6 | 1.0 | 4 | 2.5730 | 1.7153 | 1.1 | 4.35 | 45 | 45 | 30 | 45 | 0.028 | 0.65 | 0.63 |
| 19 | 0.3053 | 6 | 1.0 | 4 | 2.5730 | 1.7153 | 1.1 | 4.35 | 45 | 30 | 30 | 60 | — | 0.66 | — |
| 20 | 0.3053 | 6 | 1.0 | 4 | 2.5730 | 1.7153 | 1.1 | 4.35 | 45 | 0 | 30 | 90 | 0.004 | 0.67 | 0.92 |
| 3 | 0.3053 | 6 | 1.0 | 4 | 2.5730 | 1.7153 | 1.1 | 4.35 | 45 | 0 | 0 | 0(reference) | 0.001 | 0.71 | 0.73 |
| 21 | 0.3053 | 6 | 1.0 | 4 | 2.5730 | 1.7153 | 1.1 | 4.35 | 45 | 15 | 0 | 15 | 0.012 | — | — |
| 22 | 0.3053 | 6 | 1.0 | 4 | 2.5730 | 1.7153 | 1.1 | 4.35 | 45 | 30 | 0 | 30 | — | 0.70 | — |
| 23 | 0.3053 | 6 | 1.0 | 4 | 2.5730 | 1.7153 | 1.1 | 4.35 | 45 | 45 | 0 | 45 | 0.018 | 0.70 | 0.72 |
| 24 | 0.3053 | 6 | 1.0 | 4 | 2.5730 | 1.7153 | 1.1 | 4.35 | 45 | 30 | 0 | 60 | — | 0.70 | — |
| 25 | 0.3053 | 6 | 1.0 | 4 | 2.5730 | 1.7153 | 1.1 | 4.35 | 45 | 15 | 0 | 75 | 0.012 | — | — |
| 26 | 0.3053 | 6 | 1.0 | 4 | 2.5730 | 1.7153 | 1.1 | 4.35 | 45 | 0 | 0 | 90 | 0.001 | 0.71 | 0.73 |

The water drain test of the evaluation test 1 was conducted for each of experimental examples 18, 20, 21, 23, 25, and 26. The results of the water drain test are shown in Table 1 and FIG. 31 in addition to the results of experimental examples 1 and 3.

[Evaluation Test 2]

In addition, a response time of each of the sensor elements in experimental example 1, experimental examples 17 to 20, experimental example 3, experimental examples 22 to 24, and experimental example 26 was measured. The results of the measurement are shown in Table 1 and FIGS. 32 and 33. A test procedure for the responsiveness of the sensor output is as follows.

Figure 31:
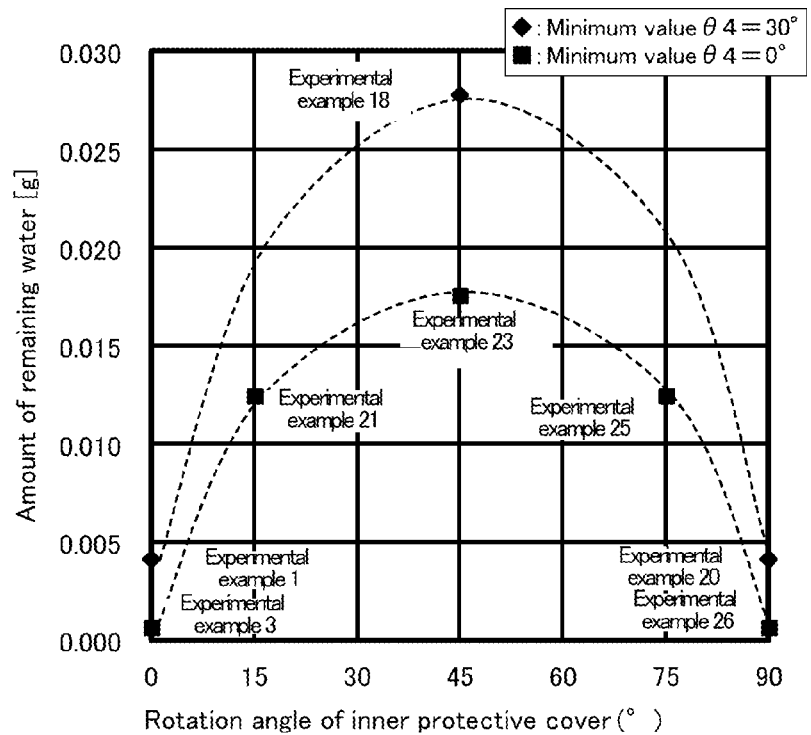
FIG. 31 is a graph illustrating a relationship between a rotation angle of the inner protective cover and an amount of remaining water.
Figure 32:
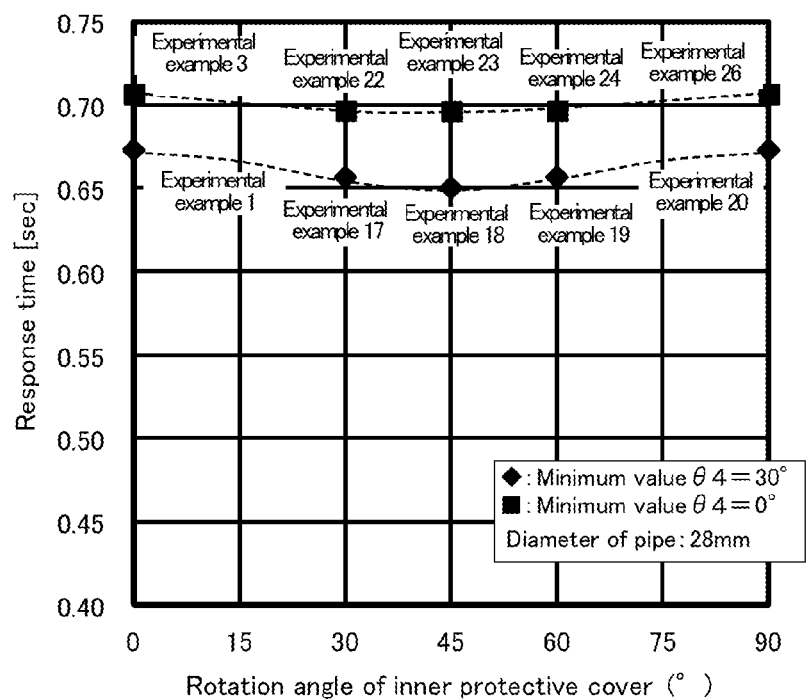
FIG. 32 is a graph illustrating a relationship between a rotation angle of the inner protective cover and a response time when the diameter of a pipe is 28 mm.
Figure 33:
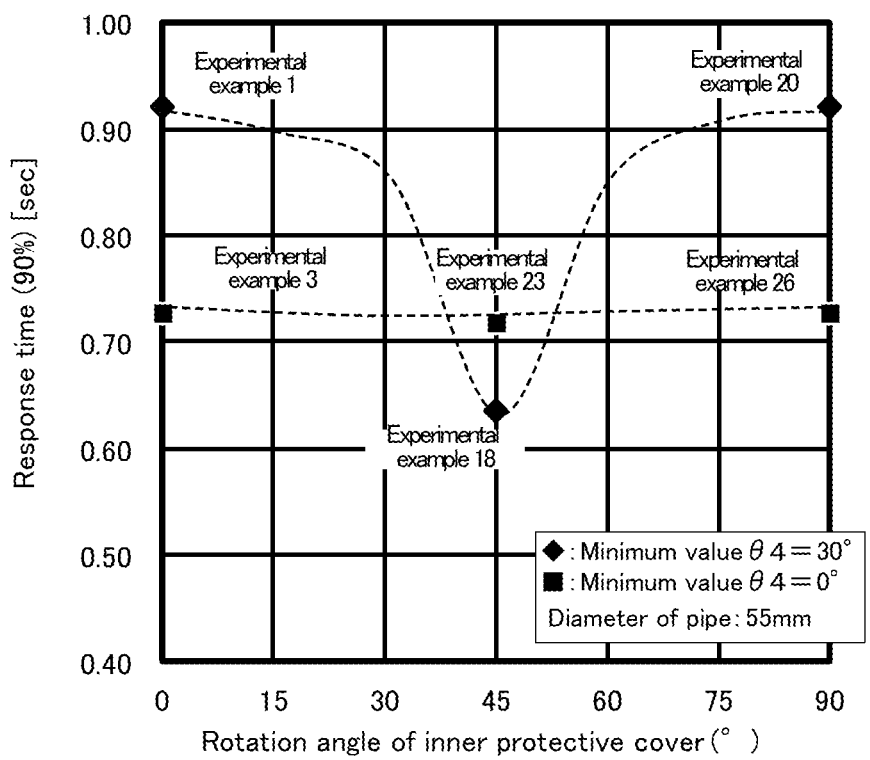
FIG. 33 is a graph illustrating a relationship between a rotation angle of the inner protective cover and a response time when the diameter of the pipe is 55 mm.

As illustrated in FIG. 1, a gas sensor is attached to the pipe 200 first. Thereafter, instead of passing exhaust gas emitted from an engine, reference gas serving as the gas to be measured was passed through the pipe 200 until the sensor output was stabilized. The reference gas was controlled so as to have an NO concentration of 70 ppm and Lambda of 1.05 by burner firing. Subsequently, oxygen was introduced into the reference gas through a gas inlet port. Thus, gas mixture having an NO concentration of 70 ppm and Lambda of 1.35 was passed through the pipe 200 until the sensor output was stabilized. Thus, the sensor element 110 functioned as an oxygen concentration cell and, therefore, an electro motive force was generated. Accordingly, the sensor output rose. At that time, a time period t10 from when the oxygen was introduced into the FIG. 31 is a graph illustrating a relationship between the rotation angle of the inner protective cover and the amount of remaining water. FIG. 32 is a graph illustrating a relationship between the rotation angle of the inner protective cover and the response time when the diameter of the pipe is 28 mm. FIG. 33 is a graph illustrating a relationship between the rotation angle of the inner protective cover and the response time when the diameter of the pipe is 55 mm. As can be seen from Table 2 and FIG. 31, when the rotation angle of the inner protective cover is 45° (when the minimum value θ3 is 45°), the value of the amount of remaining water reaches a maximum value (a peak value). As the rotation angle of the inner protective cover increases or decreases from 45° (as the minimum value θ3 decreases from 45°), the amount of remaining water decreases. In addition, the amount of remaining water in experimental examples 3, 21, 23, 25, and 26 in which the minimum value θ4 is 0° is generally smaller than that in experimental examples 1, 18, and 20 in which the minimum value θ4 is 30°. A comparison of experimental examples in which the minimum values θ3 are the same indicates that the amount of remaining water in experimental example in which the minimum value θ4 is closer to 0° is smaller than that in another experimental example.

As can be seen from Table 2 and FIG. 32, the response time in experimental examples 1, 17, 18, 19, and 20 in which the minimum value θ4 is 30° is shorter than that in experimental examples 3, 22, 23, 24, and 26 in which the minimum value θ4 is 0°. In contrast, the increase ratio of a response time in experimental examples 3, 22, 23, 24, and 26 to that in experimental examples 1, 17, 18, and 19 is relatively lower than the increase ratio of an amount of remaining water in experimental examples 3, 22, 23, 24, and 26 to that in experimental examples 1, 17, 18, and 19. In addition, as can be seen from Table 2 and FIG. 33, when the diameter of the pipe is 55 mm, the response time in experimental examples 3, 23, and 26 in which the minimum value θ4 is 0° is shorter than that in experimental examples 1 and 20 in which the minimum value θ4 is 30°, with the exception of experimental example 18. As can be seen from these results, unlike a well-known trade-off relationship between a decrease in the amount of remaining water (a prevention level of adhesion of water to a sensor element) and an increase in the response time (improvement of a sensor responsiveness), if the minimum value θ4 is close to 0°, adhesion of water to a sensor element can be more effectively prevented while preventing a decrease in the sensor responsiveness or improving the sensor responsiveness, Note that experimental examples 1 to 10, experimental examples 12 to 15, and experimental examples 17 to 26 correspond to the examples of the present invention, while experimental examples 11 and 16 correspond to comparative examples of the present invention.

Comparative Example 1

Figure 34:
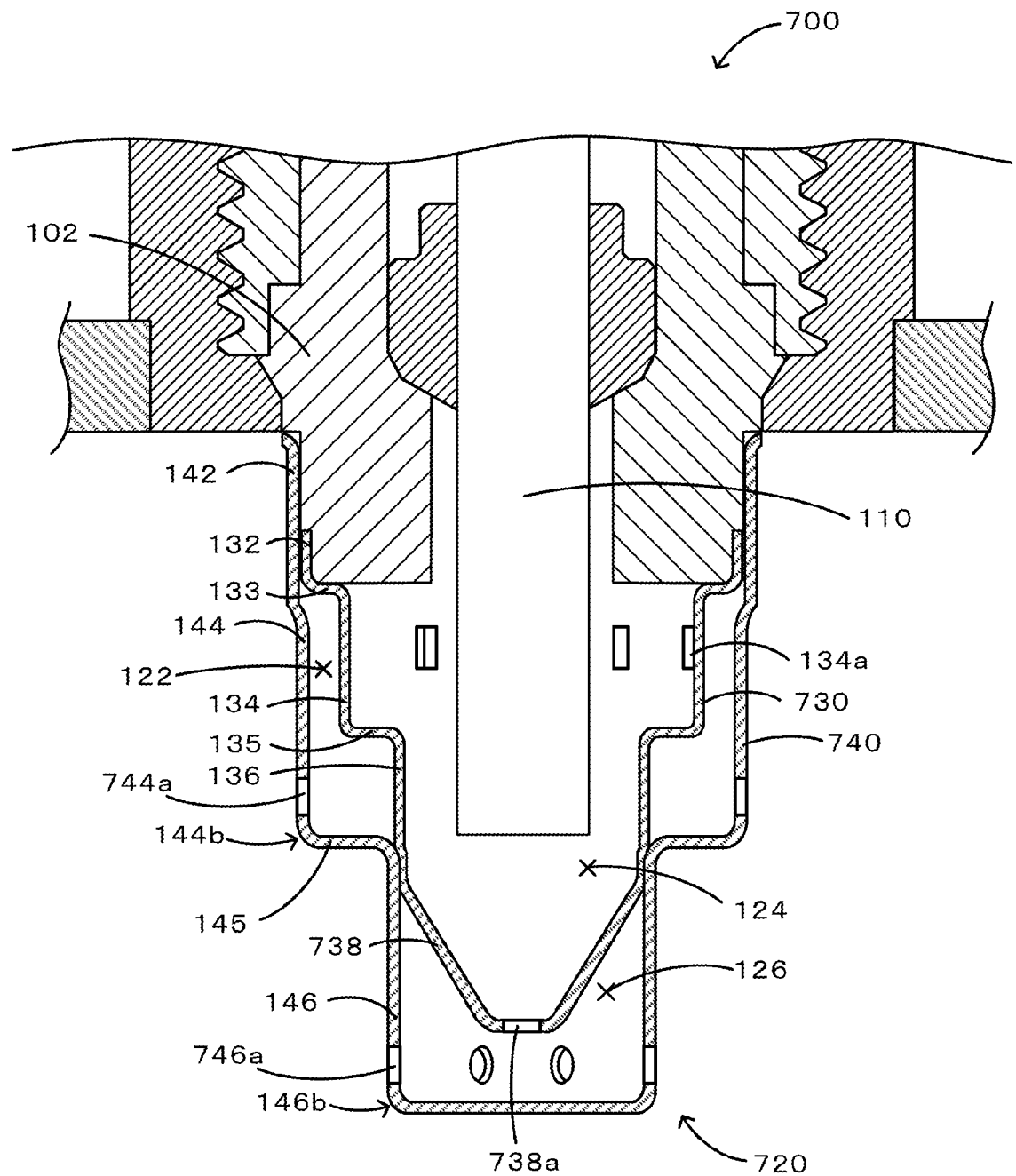
FIG. 34 is a vertical cross-sectional view illustrating the structure of a gas sensor 700 according to comparative example 1.

A plurality of gas sensors 700 illustrated in FIG. 34 were produced. Each of the gas sensors 700 includes an inner protective cover 730 and an outer protective cover 740 those serve as a protective cover 720. The inner protective cover 730 has a structure that is similar to the structure of the inner protective cover 130 illustrated in FIG. 2 with the exception that the shapes of a free end portion 738 and a second inner gas hole 738*a* differ from those of the free end portion 138 and the second inner gas holes 138*a*, respectively, and, in addition, the inner protective cover 730 does not have the stepped portion 137. Accordingly, the same numbering is used for the components other than the free end portion 738 and the second inner gas hole 738*a* as in FIG. 2 and, therefore, detailed description of the components is not provided. Unlike the free end portion 138, the free end portion 738 has a shape of an upside-down truncated triangular pyramid. The inner diameter of a portion connected to the second body portion 136 is 7.4 mm. The diameter of the bottom surface is 2.4 mm. In addition, the second inner gas hole 738*a* is a circular hole located at the central point of the bottom surface of the free end portion 738. The second inner gas hole 738*a* has an inner diameter of 1 mm. The outer protective cover 740 is similar to the outer protective cover 140 illustrated in FIG. 2 with the exception of a gas passing hole 744*a* and an outer gas hole 746*a*. Accordingly, the same numbering is used for the components other than the gas passing hole 744*a* and the outer gas hole 746*a* as in FIG. 2 and, therefore, detailed description of the components is not provided. The gas passing hole 744*a* is located in the side surface of the body portion 144, and the outer gas hole 746*a* is located in the side surface of the free end portion 146. Note that as in experimental example 1, six gas passing holes 744*a* and six outer gas holes 746*a* are formed at equal intervals.

[Evaluation Test 3]

Figure 35:
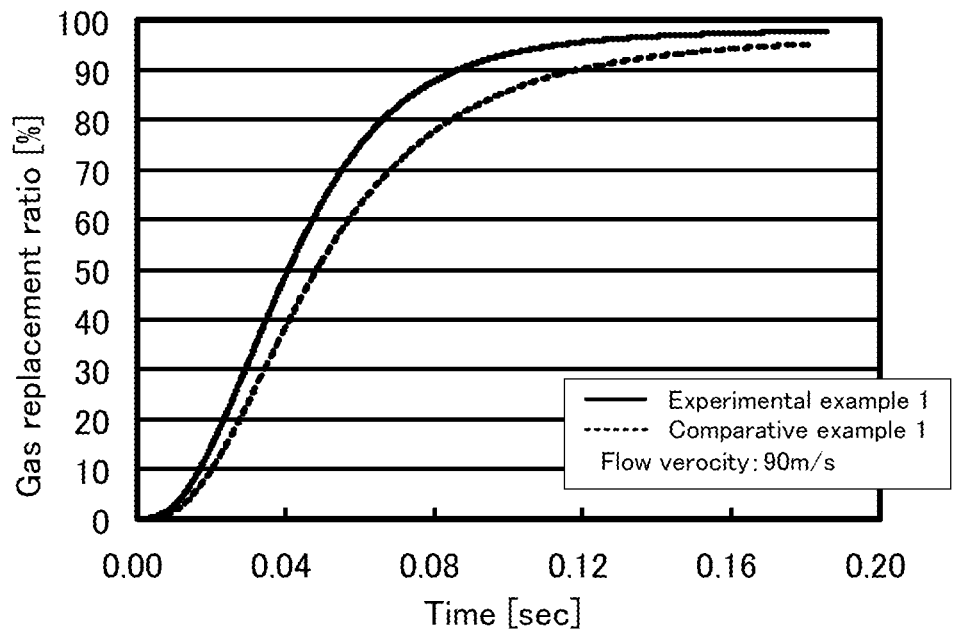
FIG. 35 is a graph illustrating a time variation of the gas replacement ratio when the flow velocity is 90 m/s.
Figure 36:
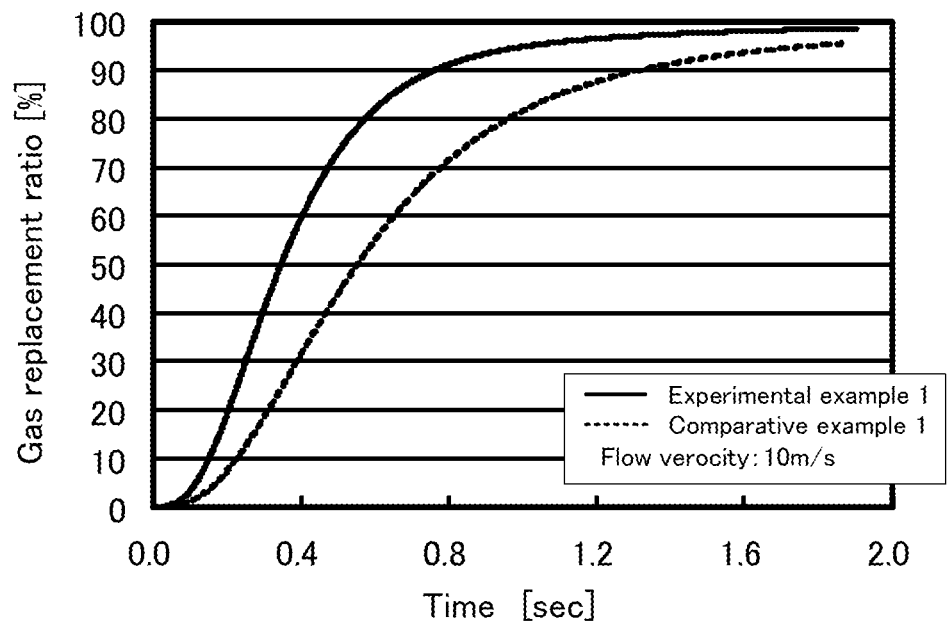
FIG. 36 is a graph illustrating a time variation of the gas replacement ratio when the flow velocity is 10 m/s.

A flow velocity dependency test was conducted for experimental example 1 and comparative example 1 in order to study a relationship between the flow velocity of the gas to be measured and the responsiveness of the sensor element. The results are shown in FIGS. 35 and 36. The flow velocity dependency test was conducted in the following manner.

As in FIG. 1, a gas sensor of each of experimental example 1 and comparative example 1 was attached to the pipe. Note that the pipe was filled with air. Air flow in the pipe was prevented for 310 seconds. Thereafter, the gas to be measured was passed in the pipe at a predetermined flow velocity. At that time, a time variation of the output of the sensor element was measured. When the output of the sensor element reached the maximum value, it was determined that the air in the protective cover was fully replaced with the gas to be measured. Then, the ratio of the output of the sensor element to the maximum value was computed as a gas replacement ratio in the protective cover. Such a gas replacement ratio was used for the time variation of the gas replacement ratio. The time variation of the gas replacement ratio was obtained for each of the case in which the predetermined flow velocity of the gas to be measured was set to 90 m/s and the case in which the predetermined flow velocity of the gas to be measured was set to 10 m/s. As the difference between the time variations of the gas replacement ratio at the flow velocities of 90 m/s and 10 m/s decreases, the flow velocity dependency decreases. Thus, even when the flow velocity decreases, the responsiveness tends not to decrease.

FIG. 35 is a graph illustrating a time variation of the gas replacement ratio when the flow velocity of the gas to be measured is 90 m/s. FIG. 36 is a graph illustrating a time variation of the gas replacement ratio when the flow velocity of the gas to be measured is 10 m/s. As can be seen from FIGS. 34 and 35, the gas replacement ratio in experimental example 1 more rapidly rises than that in comparative example 1 regardless of the flow velocity. In addition, in comparative example 1, the rise of the gas replacement ratio in the case of a flow velocity of 10 m/s is more slowed down as the time passes than in the case of a flow velocity of 90 m/s. In contrast, in experimental example 1, a time variation of the gas replacement ratio is smaller than in comparative example 1 in both cases of the flow velocities of 90 m/s and 10 m/s. That is, since, in experimental example 1, the gas passing hole is formed in the first corner portion 144*b* and the outer gas hole is formed in the second corner portion 146*b*, the flow velocity dependency can be more reduced than in comparative example 1 in which the gas passing hole and the outer gas hole are formed in the side surfaces.

The present application claims priority from Japanese Patent Application No. 2011-253165 filed on Nov. 18, 2011, and Japanese Patent Application No. 2012-249206 filed on Nov. 13, 2012, the entire contents of which are incorporated herein by reference.

What is claimed is:

1. A gas sensor comprising:
    a sensor element having a free end and a base end remote from the free end;
    an inner protective cover having a bottomed cylindrical shape and having a side surface and a bottom surface, the inner protective cover having at least one first inner gas hole and at least one second inner gas hole formed therein and covering the free end of the sensor element, each second inner gas hole being formed in the side surface or said bottom surface of the inner protective cover; and
    an outer protective cover having a bottomed cylindrical shape, the outer protective cover having a plurality of outer gas holes formed therein and covering the inner protective cover;
    wherein the first inner gas hole is located so as to be closer to the base end of the sensor element than the second inner gas hole, and wherein a ratio A2/A1 defined by a ratio of an opening area A1 per first inner gas hole and an opening area A2 per second inner gas hole is higher than or equal to 0.9 and lower than or equal to 3.8,
    wherein the outer protective cover is a cover having a side surface and a bottom surface, wherein each of the outer gas holes is formed in a boundary portion between the side surface and the bottom surface of the outer protective cover, and wherein an angle θ1 formed by an external opening plane of the outer gas hole and the bottom surface of the outer protective cover is in the range from 10° to 80°.

2. The gas sensor according to claim 1,
wherein the ratio A2/A1 is higher than or equal to 1.5 and lower than or equal to 1.9.

3. The gas sensor according to claim 1,
wherein a ratio B2/B1 defined by a ratio of a total opening area B1 of the first inner gas hole and a total opening area B2 of the second inner gas hole is higher than or equal to 0.85.

4. The gas sensor according to claim 1,
wherein a distance L between the center of the second inner gas hole and a bottom surface of the inner protective cover is less than or equal to 3 mm.

5. The gas sensor according to claim 1,
wherein a distance L between the center of the second inner gas hole and a bottom surface of the inner protective cover is less than or equal to 2.2 mm.

6. The gas sensor according to claim 1,
wherein the inner protective cover includes a guide portion that regulates a flow of a gas to be measured flowing into the inner protective cover through the first inner gas hole, and wherein a ratio R2/R1 defined by a ratio of a radius R1 representing a radius of a circumscribed circle of the sensor element, where the circumscribed circle is coaxial with the inner protective cover, and a radius R2 representing a radius of an inscribed circle of a plane including a regulation surface of the guide portion that regulates the flow of the gas to be measured, where the inscribed circle is coaxial with the inner protective cover, is higher than or equal to 1 and lower than or equal to 2.38.

7. The gas sensor according to claim 1,
wherein the gas sensor is fixed to an inside of a pipe such that a center axis of the inner protective cover is tilted from the vertical direction at an angle θ2 (0°<θ2<90°), and wherein when the second inner gas hole is projected onto a plane perpendicular to the center axis of the inner protective cover, a minimum value θ3 of an angle formed by a line extending between the center of the second inner gas hole and the center of the inner protective cover and a vertical line obtained by projecting a line extending from the center of the inner protective cover in the vertical downward direction onto the plane is greater than or equal to 0° and less than 45°.

8. The gas sensor according to claim 7,
wherein the minimum value θ3 is greater than or equal to 0° and less than or equal to 15°.

9. The gas sensor according to claim 7, further comprising:
a housing fixed to the inside of the pipe using a fixing member, the housing fixing the inner protective cover;

wherein a phase of the inner protective cover relative to the fixing member in the circumferential direction is defined so that the minimum value θ3 is set to a predetermined value by defining a fixed position of the housing relative to the fixing member using a pair of positioning portions, one formed in the housing and the other formed in the fixing member, and defining a fixed position of the inner protective cover relative to the housing using a pair of positioning portions, one formed in the inner protective cover and the other formed in the housing.

10. The gas sensor according to claim 1,
wherein the gas sensor is fixed to the inside of the pipe such that the center axis of the inner protective cover is tilted from the vertical direction at an angle θ2 (0°<θ2<90°), and wherein when each of the outer gas holes is projected onto a plane perpendicular to the center axis of the outer protective cover, a minimum value θ4 of an angle formed by a line extending between the center of the outer gas hole and the center of the outer protective cover and a vertical line obtained by projecting a line extending from the center of the outer protective cover in the vertical downward direction onto the plane is greater than or equal to 0° and less than or equal to 30°.

11. The gas sensor according to claim 10, further comprising:
a housing fixed to the inside of the pipe using a fixing member, the housing fixing the outer protective cover;

wherein a phase of the outer protective cover relative to the fixing member in the circumferential direction is defined so that the minimum value θ4 is set to a predetermined value by defining a fixed position of the housing relative to the fixing member using a pair of positioning portions, one formed in the housing and the other formed in the fixing member, and defining a fixed position of the outer protective cover relative to the housing using a pair of positioning portions, one formed in the outer protective cover and the other formed in the housing.

12. The gas sensor according to claim 1, further comprising:
a first gas chamber; and
a second gas chamber;

wherein the outer protective cover includes a cylindrical body portion having a plurality of gas passing holes formed therein, a bottomed cylindrical free end portion having a diameter that is smaller than that of the body portion, and a stepped portion that connects the body portion to the free end portion, and wherein each of the outer gas holes is a hole formed in the free end portion, and wherein the first gas chamber is surrounded by the body portion and the stepped portion of the outer protective cover and the inner protective cover, and the first gas chamber communicates with the inside of the inner protective cover through the first inner gas hole, and wherein the second gas chamber is surrounded by the free end portion of the outer protective cover and the inner protective cover, the second gas chamber does not directly communicate with the first gas chamber, and the second gas chamber communicates with the inside of the inner protective cover through the second inner gas hole.

13. The gas sensor according to claim 1,
wherein the inner protective cover includes a cylindrical first body portion having the first inner gas hole formed therein, a cylindrical second body portion, a bottomed cylindrical free end portion having the second inner gas hole formed therein, a first stepped portion that connects the first body portion to the second body portion, and a second stepped portion that connects the second body portion to the free end portion, and wherein the free end of the sensor element is located in a space surrounded by the first body portion.

* * * * *